US010576078B2

(12) United States Patent
Sanyal et al.

(10) Patent No.: US 10,576,078 B2
(45) Date of Patent: Mar. 3, 2020

(54) COMBINATION OF CLOFAZIMINE AND IMATINIB FOR EFFECTIVE THERAPY OF DRUG-RESISTANT MYELOID LEUKEMIA

(71) Applicant: Council of Scientific & Industrial Research, New Delhi (IN)

(72) Inventors: Sabyasachi Sanyal, Uttar Pradesh (IN); Harish Kumar, Uttar Pradesh (IN); Naibedya Chattopadhyay, Uttar Pradesh (IN); Ravishankar Ramachandran, Uttar Pradesh (IN); Arun Kumarv Trivedi, Uttar Pradesh (IN); Sonal Shree, Uttar Pradesh (IN); Anagha Ashok Gurjar, Uttar Pradesh (IN); Sourav Chattopadhyay, Uttar Pradesh (IN); Sapana Kushwaha, Uttar Pradesh (IN); Abhishek Kumar Singh, Uttar Pradesh (IN); Shikha Dubey, Uttar Pradesh (IN); Kiran Lata, Uttar Pradesh (IN); Riyazuddin Mohammed, Uttar Pradesh (IN); Jiaur Rahaman Gayen, Uttar Pradesh (IN); Anil Kumar Tripathi, Uttar Pradesh (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 16/117,156

(22) Filed: Aug. 30, 2018

(65) Prior Publication Data
US 2019/0350928 A1 Nov. 21, 2019

(30) Foreign Application Priority Data
Aug. 30, 2017 (IN) .............................. 201711030707

(51) Int. Cl.
A61K 31/498 (2006.01)
A61K 31/496 (2006.01)
A61K 31/513 (2006.01)
A61K 31/506 (2006.01)
A61P 35/02 (2006.01)

(52) U.S. Cl.
CPC .......... *A61K 31/498* (2013.01); *A61K 31/506* (2013.01); *A61P 35/02* (2018.01)

(58) Field of Classification Search
CPC ... A61K 31/498; A61K 31/496; A61K 31/513
USPC ................................ 514/250, 252.13, 269
See application file for complete search history.

(56) References Cited
U.S. PATENT DOCUMENTS
8,669,257 B2 3/2014 Liu et al.

OTHER PUBLICATIONS

Bartram, et al.;Translocation of c-abl oncogene correlates with the presence of a Philadelphia chromosome in chronic myelocytic leukaemia; Nature; (306); 277-280; Nov. 17, 1983. US.
Shtivelman, et al.; Fused transcript of abl and bcr genes in chronic myelogenous leukaemia; Nature; (315); 550-554; 1985. US.
Lugo, et al.;Tyrosine Kinase Activity and Transformation Potency of bcr-abl Oncogene Products; Science; (247); 1079-1082; 1990. US.
An, et al.;BCR-ABL tyrosine kinase inhibitors in the treatment of Philadelphia chromosome positive chronic myeloid leukemia: A review; Leuk Res; (34); 1255-1268; 2010. US.
Prost, et al.; Erosion of the chronic myeloid leukaemia stem cell pool by PPARγ agonists; Nature; (525); 380-383; 2015. US.
Glodkowska-Mrowka, et al.; PPARγ ligands increase antileukemic activity of second- and third-generation tyrosine kinase inhibitors in chronic myeloid leukemia cells; Blood Cancer J; (6); e377; 2016. PL
Tuccori, et al.;Pioglitazone use and risk of bladder cancer: population based cohort study; BMJ; (352); i1541; 2016. US.
Nissen, et al.;Effect of Rosiglitazone on the Risk of Myocardial Infarction and Death from Cardiovascular Causes; N Engl J Med; (356); 2457-2471; 2007. US.
Gopal, et al.; Systematic review of clofazimine for the treatment of drug-resistant tuberculosis; Int J Tuberc Lung Dis; (17); 1001-1007; 2013. US.
Cholo, Steel, Fourie, Germishuizen and Anderson; Clofazimine: current status and future prospects; J Antimicrob Chemother; (67); 290-298; 2012. US.
Ren, et al.;Clofazimine Inhibits Human Kv1.3 Potassium Channel by Perturbing Calcium Oscillation in T Lymphocytes; PLoS One; (3); e4009; 2008. US.
Leanza, et al;Clofazimine, Psora-4 and PAP-1, inhibitors of the potassium channel Kv1.3, as a new and selective therapeutic strategy in chronic lymphocytic leukemia; Leukemia; (27); 1782-1785; 2013. US.
Leanza, et al.; Inhibitors of mitochondrial Kv1.3 channels induce Bax/Bak-independent death of cancer cells; EMBO Mol Med; (4); 577-593; 2012. US.
Smith, et al.; Functional Up-regulation of HERG K Channels in Neoplastic Hematopoietic Cells; J Biol Chem; (277); 18528-18534; 2002. US.
Yawalkar, et al.; Lamprene ( Cl ofaz imine) in Leprosy; Lepr Rev; (50); 135-144; 1979. US.

(Continued)

*Primary Examiner* — Raymond J Henley, III
(74) *Attorney, Agent, or Firm* — Belles Katz LLC

(57) ABSTRACT

The present invention relates to method of treating chronic myeloid leukemia (CML) or drug resistant CML comprising, administering to human being or any other mammal or animal in need thereof, a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI). The invention also provides the kit for treatment of CML or drug resistant CML.

16 Claims, 32 Drawing Sheets
Specification includes a Sequence Listing.

(56) References Cited

OTHER PUBLICATIONS

O'Connor, et al.; The Pharmacology, Metabolism, and Chemistry of Clofazimine; Drug Metab Rev; (27); 591-614; 1995. US.

Marcato, et al.; Aldehyde dehydrogenase: Its role as a cancer stem cell marker comes down to the specific isoform; Cell Cycle; (10); 1378-1384; 2011. US.

Groffen, et al.; Philadelphia Chromosomal Breakpoints Are Clusterd within a Limited Region, bcr, on Chromosome 22; Cell; (36); 93-99; 1984. US.

Brandt; Reduced Number of Peripheral Blood Granulocytes in Chronic Myeloid Leukaemia during Administration of Clofazimine (B 663); Scand J Haematol; (9); 159-166; 1972. US.

Schaad-Lanyi, et al.; Pharmacokinetics of Clofazimine in Healthy Volunteers; Int J Lepr Other Mycobact Dis; (55); 9-15; 1987. US.

| CFZ (µM) | IMT (µM) | Effect | CI |
|---|---|---|---|
| 1.56 | 5.00E-07 | 0.89 | 46.68 |
| 1.56 | 1E-06 | 0.78 | 4.371 |
| 1.56 | 0.00001 | 0.71 | 1.511 |
| 1.56 | 0.0001 | 0.44 | 0.058 |
| 1.56 | 0.001 | 0.38 | 0.03 |
| 1.56 | 0.01 | 0.22 | 0.006 |
| 1.56 | 0.1 | 0.19 | 0.019 |
| 1.56 | 0.25 | 0.18 | 0.037 |
| 1.56 | 0.5 | 0.17 | 0.061 |
| 1.56 | 1 | 0.15 | 0.079 |
| 1.56 | 1.56 | 0.15 | 0.123 |
| 1.56 | 3.12 | 0.14 | 0.196 |
| 1.56 | 6.25 | 0.13 | 0.308 |
| 1.56 | 12.5 | 0.12 | 0.476 |
| 1.56 | 25 | 0.09 | 0.385 |

FIG. 4B

| CFZ (µM) | Dasa (µM) | Effect | CI |
|---|---|---|---|
| 1.56 | 5.00E-07 | 0.94 | 311.07 |
| 1.56 | 0.000001 | 0.91 | 88.509 |
| 1.56 | 0.00001 | 0.89 | 46.686 |
| 1.56 | 0.0001 | 0.74 | 2.331 |
| 1.56 | 0.001 | 0.62 | 0.485 |
| 1.56 | 0.01 | 0.54 | 0.248 |
| 1.56 | 0.1 | 0.27 | 0.051 |
| 1.56 | 0.25 | 0.24 | 0.081 |
| 1.56 | 0.5 | 0.19 | 0.079 |
| 1.56 | 1 | 0.16 | 0.097 |
| 1.56 | 1.56 | 0.15 | 0.126 |
| 1.56 | 3.12 | 0.14 | 0.208 |
| 1.56 | 6.25 | 0.07 | 0.069 |
| 1.56 | 12.5 | 0.06 | 0.095 |
| 1.56 | 25 | 0.04 | 0.07 |

FIG. 4C

| Parameter (Unit) | Imatinib | Imatinib in [Clofazimine + Imatinib mesylate] |
|---|---|---|
| $C_{max}$ (ng/mL) | 201.51 ± 18.98 | 541.95 ± 59.52 |
| $AUC_{0-t}$ (h*µg/mL) | 1.81 ± 0.33 | 3.8 ± 0.82 |
| $T_{max}$ (h) | 4 | 4 |
| $T_{1/2}$ (h) | 5.49 ± 0.32 | 6.04 ± 1.63 |
| Cl (L/hr/Kg) | 26.26 ± 4.7 | 12.66 ± 2.74 |
| % $F_r$ | - | 209.26 ± 45.64 |

FIG. 7C

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:

<223> OTHER INFORMATION: Forward Primer Sequence

<400> SEQUENCE: 1
tggttctcct tcgaactgct                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse Primer Sequence

<400> SEQUENCE: 2
caatgcgatg gtcaagacac                                              20

<210> SEQ ID NO 3
<211> LENGTH: 21
<212> TYPE: DNA
<213> ORGANISM: Artificial Sequence
<220> FEATURE:
<223> OTHER INFORMATION: Forward Primer Sequence

<400> SEQUENCE: 3
gcagggggga gccaaaaggg t                                            21

<210> SEQ ID NO 4
<211> LENGTH: 21
<212> TYPE: DNA
<213> ORGANISM: Artificial Sequence
<220> FEATURE:
<223> OTHER INFORMATION: Reverse Primer Sequence

<400> SEQUENCE: 4
tgggtggcag tgatggcatg g                                            21

<210> SEQ ID NO 5
<211> LENGTH: 19
<212> TYPE: DNA
<213> ORGANISM: Artificial Sequence
<220> FEATURE:
<223> OTHER INFORMATION: Forward Primer Sequence

<400> SEQUENCE: 5
tgaaggccac catcatcag                                               19

<210> SEQ ID NO 6
<211> LENGTH: 20
<212> TYPE: DNA
<213> ORGANISM: Artificial Sequence
<220> FEATURE:
<223> OTHER INFORMATION: Reverse Primer Sequence

<400> SEQUENCE: 6
tgttcaagat ctcgccactg                                              20

<210> SEQ ID NO 7
<211> LENGTH: 23
<212> TYPE: DNA
<213> ORGANISM: Artificial Sequence
<220> FEATURE:
<223> OTHER INFORMATION: Forward Primer Sequence

<400> SEQUENCE: 7
tttttcaagc agtaggaatt gga                                          23

-continued

```
<210> SEQ ID NO 8
<211> LENGTH: 23
<212> TYPE: DNA
<213> ORGANISM: Artificial Sequence
<220> FEATURE:
<223> OTHER INFORMATION: Reverse Primer Sequence

<400> SEQUENCE: 8
gtgatgtagt agctgcatga tcg                                              23

<210> SEQ ID NO 9
<211> LENGTH: 24
<212> TYPE: DNA
<213> ORGANISM: Artificial Sequence
<220> FEATURE:
<223> OTHER INFORMATION: Forward Primer Sequence

<400> SEQUENCE: 9
gacagaatca cagaactgat tggt                                             24

<210> SEQ ID NO 10
<211> LENGTH: 21
<212> TYPE: DNA
<213> ORGANISM: Artificial Sequence
<220> FEATURE:
<223> OTHER INFORMATION: Reverse Primer Sequence

<400> SEQUENCE: 10
cgcatggtag aattcatagg c                                                21

<210> SEQ ID NO 11
<211> LENGTH: 21
<212> TYPE: DNA
<213> ORGANISM: Artificial Sequence
<220> FEATURE:
<223> OTHER INFORMATION: Forward Primer Sequence

<400> SEQUENCE: 11
tcactttcaa gttggctgtc c                                                21

<210> SEQ ID NO 12
<211> LENGTH: 25
<212> TYPE: DNA
<213> ORGANISM: Artificial Sequence
<220> FEATURE:
<223> OTHER INFORMATION: Reverse Primer Sequence

<400> SEQUENCE: 12
cattccacac cctattatca tctgt                                            25

<210> SEQ ID NO 13
<211> LENGTH: 19
<212> TYPE: DNA
<213> ORGANISM: Artificial Sequence
<220> FEATURE:
<223> OTHER INFORMATION: Forward Primer Sequence

<400> SEQUENCE: 13
agccacatcg ctcagacac                                                   19

<210> SEQ ID NO 14
<211> LENGTH: 19
<212> TYPE: DNA
<213> ORGANISM: Artificial Sequence
<220> FEATURE:
<223> OTHER INFORMATION: Reverse Primer Sequence
```

```
<400> SEQUENCE: 14
gcccaatacg accaaatcc                                                              19
```

COMBINATION OF CLOFAZIMINE AND IMATINIB FOR EFFECTIVE THERAPY OF DRUG-RESISTANT MYELOID LEUKEMIA

CROSS-REFERENCE TO RELATED APPLICATIONS

This application claims priority to Indian Patent Application No. 201711030707, filed Aug. 30, 2017, the entirety of which is incorporated herein by reference.

REFERENCE TO SEQUENCE LISTING

Applicants assert that the paper copy of the Sequence Listing is identical to the Sequence Listing in computer readable form found on the accompanying computer file. Applicants incorporate the contents of the sequence listing by reference in its entirety.

FIELD OF THE INVENTION

The present invention relates to Clofazimine (CFZ), or its derivative, analogue, salt thereof as a leukemia stem cell inhibitory factor for use in the treatment of chronic myelogenous leukemia (CML) or BCR-ABL tyrosine kinase inhibitor (TKI) resistant CML alone or in a synergistic combination with TKIs drugs, including but not limiting to imatinib and dasatinib.

BACKGROUND OF THE INVENTION

Chronic myeloid leukemia (CML) is a myeloproliferative disorder characterized by the presence of Bcr-Abl oncogenic reciprocal translocation t(9,22)(q34:q11) (Bartram, et al.; Nature; (306); 277-280; 1983). This translocation is present in 90-95% of CML patients and leads to the expression of the fusion protein Bcr-Abl (P-210 kDa) with constitutive protein-tyrosine kinase activity (Shtivelman, et al.; Nature; (315); 550-554; 1985, Groffen, et al.; Cell; (36); 93-99; 1984). Bcr-Abl is essential for malignant transformation and triggers several cellular signaling pathways (e.g. CrkL, STAT5, PI3K/AKT) to regulate cell proliferation, differentiation, migration, survival and DNA repair (Lugo, et al.; Science; (247); 1079-1082; 1990). Targeting Bcr-Abl has become an important strategy for CML treatment (An, et al.; Leuk Res; (34); 1255-1268; 2010). Imatinib (STI571, Gleevec, Norvartis) effectively inhibits tyrosine kinase activity by occupying the adenosine triphosphate (ATP)-binding pocket of Bcr-Abl, thus abrogating subsequent signal transduction and is the preferred first-line therapy for CML (An, et al.; Leuk Res; (34); 1255-1268; 2010).

Although, treatment for CML has seen tremendous advance following the discovery of imatinib and other BCR-ABL tyrosine kinase inhibitors (TKI), however, complete molecular response, amounting to undetectable BCR-ABL transcript is not achieved in majority of the CML patients (Prost, et al.; Nature; (525); 380-383; 2015). TKI-resistance can occur due to mutations in BCR-ABL, however, in approximately 50% cases BCR-ABL-independent mechanisms including TKI-refractory leukemia stem cells (LSC) contribute to resistance, recurrence and disease progression (Prost, et al.; Nature; (525); 380-383; 2015). Recently, anti-diabetic thiazolidinedione peroxisome proliferator-activated receptor gamma (PPARγ) agonists; pioglitazone in particular, was reported to erode quiescent LSCs by targeting signal transducer and activator of transcription 5 (stat5) expression in preclinical and clinical settings (Prost, et al.; Nature; (525); 380-383; 2015, Glodkowska-Mrowka, et al.; Blood Cancer J; (6); e377; 2016). Unfortunately, recently found association of pioglitazone with bladder cancer (Tuccori, et al.; BMJ; (352); i1541; 2016) led to its withdrawal in France and Germany. Rosiglitazone, on the contrary did not increase bladder cancer incidence, but is associated with severe cardiovascular risks (Nissen, et al.; N Engl J Med; (356); 2457-2471; 2007).

Clofazimine (CFZ) is a riminophenazine leprosy drug which is also effective against multidrug-resistant and extremely drug-resistant tuberculosis (Gopal, et al.; Int J Tuberc Lung Dis; (17); 1001-1007; 2013). CFZ imparts its anti-bacterial actions by generation of reactive oxygen species (ROS), particularly superoxides and $H_2O_2$ (Cholo, et al.; J Antimicrob Chemother; (67); 290-298; 2012). CFZ also displays anti-inflammatory properties that is important for its antileprosy effects including suppression of erythema nodosum leprosum and leprosy-associated immune reactions (Cholo, Steel, Fourie, Germishuizen and Anderson; J Antimicrob Chemother; (67); 290-298; 2012). Clinical studies have also found CFZ to be effective against various autoimmune diseases including discoid lupus erythematosus, Crohn's disease, ulcerative colitis, psoriasis, Meischer's granuloma and graft-versus-host disease (Ren, et al.; PLoS One; (3); e4009; 2008). CFZ is reported to impart its immonomodulatory activities by blocking KV1.3 voltage gated potassium channel (Ren, et al.; PLoS One; (3); e4009; 2008) and thereby inhibit chronic lympocytic leukemia cells (Leanza, et al.; EMBO Mol Med; (4); 577-593; 2012, Leanza, et al.; Leukemia; (27); 1782-1785; 2013) and based on its KV1.3 modulatory properties CFZ and its derivatives have been patented for various autoimmune diseases (Liu et al, U.S. Pat. No. 8,669,257 B2). CFZ has also been evaluated in chronic myeloid leukemia patients and was found to reduce granulocytes, basophilic leucocytes and histamine in peripheral blood of these patients (Brandt; Scand J Haematol; (9); 159-166; 1972). However, this report does not elucidate if the beneficial effects of CFZ was routed through direct apoptosis/differentiation-inducing effects of CFZ on CML cells or simply an indirect outcome of its immunomodulatory activities. Further, CFZ has not been tested in BCR-ABL TKI-inhibitor-resistant CML cells and its effect in LSCs or quiescent LSCs alone or in combination with BCR-ABL TKI inhibitors is not known. Furthermore, no report is available in public domain where the ability of CFZ to alter the bioavailability of TKI inhibitors has been investigated.

OBJECTS OF THE INVENTION

The first objective of this invention is to provide a method of treating chronic myeloid leukemia (CML) or drug resistant CML comprising, administering to human being or any other mammal or animal in need thereof, a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI).

The second objective of this invention is to provide a combination comprising a therapeutically effective amount of Clofazimine (CFZ) or its pharmaceutically acceptable derivative, analogue, salt or composition and a tyrosine kinase inhibitor (TKI), or its pharmaceutically acceptable salt or composition, for treating chronic myeloid leukemia (CML) or drug resistant CML.

Another objective of the invention is to provide CFZ or its pharmaceutically acceptable derivative, analogue or salt as a treatment of CML or drug resistant CML in combination with TKIs including but not limiting to imatinib and dasatinib.

Still another objective of the present invention is to provide a dosage regimen and a mode of administration of CFZ (alone) or its pharmaceutically acceptable derivative, analogue or salt with one or more of the pharmaceutically acceptable carrier or excipient etc. or in combination with TKIs.

The dosage will vary according to the type of disorder, the disease conditions and will be subject to the judgment of the medical practitioner involved.

SUMMARY OF THE INVENTION

An embodiment of the present invention is to provide method of treating chronic myeloid leukemia (CML) or drug resistant CML comprising, administering to human being or any other mammal or animal in need thereof, a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI).

In another embodiment of the present invention, the subject is a mammal, preferably human.

In yet another embodiment of the present invention, there is provided a method for treatment of CML, wherein a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI) is administered in dose from 0.1 mg to 5000 mg, preferably from 0.5 to 1000, more preferably from 1 mg to 800 mg weekly or bi-weekly or daily or twice a day or three times a day or in still more divided doses.

In yet another embodiment of the present invention, there is provided a method for treatment of CML or drug-resistant CML, wherein a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI). is administered in a dose from 0.1 mg to 5000 mg, preferably from 0.5 to 1000, more preferably from 1 mg to 800 mg weekly or bi-weekly or daily or twice a day or three times a day or in still more divided doses in combination with TKIs including but not limiting to imatinib and dasatinib, wherein the dose of TKIs would be 0.1 mg-2000 mg, preferably from 10 mg-1800 mg, more preferably from 25 mg-1000 mg weekly or bi-weekly or daily or twice a day or three times a day or in still more divided doses.

In another embodiment of the present invention, there is provided a method for treatment or prevention of CML or drug-resistant CML, wherein a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI) is administered by a route selected from the group consisting of oral, systemic, local, topical, intravenous, intra-arterial, intra-muscular, subcutaneous, intra-peritoneal, intra-dermal, buccal, intranasal, inhalation, vaginal, rectal and transdermal.

In yet another embodiment of the present invention there is provided a method for treatment or prevention of CML or drug-resistant CML wherein, a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI). is in the form of a suspension, liquid formulation, tablet, pill, capsule, powder or granule containing at least one of the following pharmaceutically acceptable excipient:
  (i) a diluent selected from the group consisting of lactose, mannitol, sorbitol, microcrystalline cellulose, sucrose, sodium citrate and dicalcium phosphate or a combination thereof;
  (ii) a binder selected from the group consisting of gum tragacanth, gum acacia, methyl cellulose, gelatin, polyvinyl pyrrolidone and starch or a combination thereof;
  (iii) a disintegrating agent selected from the group consisting of agar-agar, calcium carbonate, sodium carbonate, silicates, alginic acid, corn starch, potato tapioca starch and primogel or a combination thereof;
  (iv) a lubricant selected from the group consisting of magnesium stearate, calcium stearate, calcium steorotes, talc, solid polyethylene glycols and sodium lauryl sulphate or a combination thereof;
  (v) a glidant such as colloidal silicon dioxide;
  (vi) a sweetening agent selected from the group consisting of sucrose, saccharin and fructose or a combination thereof;
  (vii) a flavoring agent selected from the group consisting of peppermint, methyl salicylate, orange flavor and vanilla flavor or a combination thereof;
  (viii) a wetting agent selected from the group consisting of cetyl alcohol and glyceryl monostearate or a combination thereof;
  (ix) an absorbent selected from the group consisting of kaolin and bentonite clay or a combination thereof; and
  (x) a solution retarding agent selected from the group consisting of wax and paraffin or a combination thereof.

In yet another embodiment of the present invention, there is provided a pharmaceutical acceptable composition for the treatment of CML or drug-resistant CML comprising a combination of a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI), wherein the tyrosine kinase inhibitor is selected from, but not limited to imatinib and dasatinib, or a pharmaceutically acceptable salt or a pharmaceutically acceptable composition thereof either or both are in the form of a suspension, liquid formulation, tablet, pill, capsule, powder or granule containing at least one of the pharmaceutically acceptable excipient as mentioned above:

In yet another embodiment, the combination of CFZ or its pharmaceutically acceptable derivative, analogue or salt and tyrosine kinase inhibitor (TKI) is in a ratio of 1:4.

In yet another embodiment of the present invention, there is provided a kit for the treatment chronic myeloid leukemia (CML) or drug resistant CML, the kit comprising: a composition of clofazimine or its pharmaceutically acceptable analogue, derivative, or salt; a composition comprising one or more tyrosine kinase inhibitor(s); and a pamphlet containing instruction of use; wherein the pamphlet contains instructions that administration of said compositions in combination provides synergistic effect in comparison with the administration of either clofazimine or tyrosine kinase inhibitor(s) alone in the form of tablets or capsules with a pamphlet containing instruction of use. Such a kit may be consisting of both TKIs and clofazimine tablets or capsules in a single strip or individual strips (of CFZ and TKIs) containing instructions of use.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

Abbreviations

Abl Abelson Kinase
ALDH Aldehyde Dehydrogenase
AP Acclerated phase
APC Allophycocyanin
ATP Adenosine Triphosphate
BAX Bcl-2-Associated X protein
BC Blast crisis
BCA Bicinchoninic Acid
Bcl-2 B-Cell Lymphoma-2
Bcr-Abl Bcr-Abl Fusion Gene
BSA Bovine Serum Albumin
CFZ Clofazimine
CFSE Carboxy Fluorescein Succinimidyl Ester
CITED2 Cbp/p300-Interacting Transactivator 2
CI Combination Index
CLL Chronic Lympocytic Leukemia
CML Chronic myeloid leukemia
CP Chronic Phase
CP-CML Chronic phase CML
CrkL V-Crk Avian Sarcoma Virus CT10 Oncogene Homolog-Like
DASA Dasatinib
DMSO Dimethyl Sulpoxide
DNA Deoxyribonucleic Acid
DTT Dithiothreitol
EC50 Half Maximal Effective Concentration
FD Freshly Diagnosed
FITC Fluorescein Isothiocyanate
HIF-1α Hypoxia-Inducible Factor-1α
HIF-2α Hypoxia-Inducible Factor-2α
HRP Horseradish Peroxidase
IC50 Half Maximal Inhibitory Concentration
IgG Immunoglobulin G
IMT Imatinib
KV1.3 Potassium voltage-gated channel, shaker-related subfamily, member 3
LSC Leukaemic Stem Cell
PARP Poly (ADP-Ribose) Polymerase
PBS Phosphate Buffer Saline
PBMCs Peripheral Blood Mononuclear Cells
PCR Polymerase Chain Reaction
PE Phycoerythrin
PIO Pioglitazone
PI Propidium Iodine
PMA Phorbol myristate acetate
PVDF Polyvinylidene Fluoride
PSTAT5 phospho-Signal Transducers and Activators of Transcription 5
QRT-PCR Quantitative Real Time PCR
Resp Imatinib-responder
Res Imatinib-resistant
ROS Reactive Oxygen Species
SEM Standard Error of the Mean
STAT5 Signal Transducers and Activators of Transcription 5
TdT Terminal deoxynucleotidyl transferase
TKI Tyrosine-Kinase Inhibitor
TUNEL Terminal Deoxynucleotidyl Transferase dUTP Nick End Labeling

BRIEF DESCRIPTION OF THE DRAWINGS

The present invention will become more fully understood from the detailed description and the accompanying drawings, wherein:

FIG. 1A in particular shows K562 cells do not express KV1.3 Reverse-transcriptase PCR-based detection of KV1.3 in leukemia cell lines. NC; no DNA control. Data is representative of three independent experiments.

FIG. 1B in particular shows CFZ reduces K562 cell viability in a concentration-dependent manner. K562 cells were treated with indicated concentrations of CFZ for 24 h or 48 h, cell viability was then assessed using the CellTiter-Glo luminescent cell viability assay (Promega). Data is mean±SEM of three independent experiments (each in triplicates). $IC_{50}$ was calculated using Graphpad prism 5 software.

FIGS. 1C-ID in particular show CFZ concentration-dependently induces apoptosis in K562 cells as determined by Annexin V staining. K562 cells were treated with CFZ for 48 h and apoptosis was analyzed by annexin V and propidium iodide (PI) staining followed by flow-cytometry (FACSCalibur, BD biosciences). (C) Mean±SEM of three independent experiments are plotted. (D) Representative dot plot.

FIG. 1E in particular shows CFZ induces apoptosis as determined by PARP cleavage. PARP cleavage in K562 cells was assessed by western blotting. One representative of three independent experiments is shown.

FIG. 1F in particular shows CFZ induces apoptosis as determined by Terminal deoxynucleotidyl transferase dUTP nick end labeling (TUNEL) assay. K562 cells were treated with CFZ for 48 h and TUNEL staining was performed followed by fluorescent microscopy. Images are representative of two independent experiments (8 fields per group).

FIG. 1G in particular shows CFZ induces Cytochrome C release, cleavage of caspase-3 and -9, Bax expression and downregulates Bcl2 in K562 cells. The expression of indicated proteins was determined by immunoblotting in K562 cells following indicated treatments. One representative of three independent experiments is shown.

FIGS. 1H-1I in particular show CFZ induces apoptosis in CP-CML cells. Peripheral blood mononuclear cells (PBMC; gated monocytes used in all apoptosis or differentiation studies here and henceforth) from control donors or CP-CML cells were treated with 5 μM CFZ, imatinib or dasatinib for 48 h followed by annexin V/PI staining and flow-cytometry. FD; freshly diagnosed, Resp; imatinib-responder, Res; imatinib-resistant. I. % apoptosis in CP-CML cells form imatinib-resistant patients in FIG. 1H, harboring indicated BCR-ABL mutations are plotted. p<0.01, *p<0.0001. *Vehicle (V) vs treatment, #imatinib vs other treatment groups, $dasatinib vs CFZ.

FIG. 2A in particular shows CFZ reduces CD34+ population by induction of apoptosis. CD34$^+$ population from CP-CML cells from imatinib-resistant patients (n=3) were individually purified using a CD34 microbead kit (Miltenyi Biotech) and were treated with 5 µM CFZ or salinomycin for 48 h. Cells were then divided into two groups. One group was assessed by immunostaining for CD34 and the other group was stained with annexin V/PI and the cells were then analyzed by flow-cytometry. Salinomycin was used as positive control. p<0.01, *p<0.0001.

FIG. 2B in particular shows CFZ induces apoptosis in committed CD34$^+$38$^+$ or primitive CD34$^+$38$^-$ CML progenitors. CD34$^+$ population from primary CP-CML cells from imatinib-resistant patients (n=3) were purified using a CD34 microbead kit. Cells were incubated with V or 2.5 µM CFZ for 96 h, stained with PE-conjugated anti-CD34 and FITC-conjugated anti-CD38 antibodies for specific subpopulation and apoptosis was analyzed by APC labeled annexin V and propidium iodide (PI) staining followed by flow-cytometry (FACSCalibur, BD biosciences). *p<0.05, **p<0.01.

FIG. 2C in particular shows CFZ suppresses aldehyde dehydrogenase (ALDH) activity in CP-CML cells. CP-CML cells from imatinib-resistant patients (n=6) were treated with CFZ or salinomycin (5 µM; 48 h) and aldehyde dehydrogenase activity in these cells were assessed using an ALDEFLUOR kit (Stemcell technologies). ***p<0.0001.

FIG. 2D in particular shows CFZ suppresses stat5 protein expression. K562 cells were treated as indicated for 72 h and stat5 expression was assessed by immunoblotting. Pioglitazone (Pio) was used as a positive control. Data is one representative of 3 independent experiments.

FIG. 2E in particular shows CFZ does not affect stat5 or CrkL phosphorylation. K562 cells were treated as indicated for 30 min and stat5 phosphorylation at Y694 or CrkL phosphorylation at Y207 were assessed by immunoblotting. Total stat5 or β-actin expression was assessed to ensure equal loading. Pio was used as a negative control and IMT was used as a positive control. Data is one representative of 3 independent experiments.

FIG. 2F in particular shows CFZ suppresses expression genes that are important for LSC maintenance and function. CD34$^+$ cells isolated from IMT-resistant patients (n=3) were treated with CFZ (5 µM, 24 h) and stat5b, HIF-1α, HIF-2α and CITED2 transcripts were assessed by QRT-PCR (in triplicates). ***p<0.0001.

FIG. 2G in particular shows CD34+ cells do not express KV1.3. CD34+ cells were isolated from imatinib-resistant patients (P61 indicates patient number 61 and so forth); and investigated for KV1.3 expression by reverse-transcriptase PCR (n=7). K562 and HL-60 cell lines were used as negative controls and U937 cell line was used as positive control.

FIG. 3A in particular shows CFZ induces megakaryocytic phenotype in K562 cells. K562 cells were treated with CFZ for 120 h and May-Grünwald-Giemsa staining followed by light microscopy was used to assess cellular morphology. Cells exhibiting lobulated nuclei are indicated with arrows. PMA was used as appositive control. Representative photomicrographs from two independent experiments (8 fields per treatment group) are shown.

FIG. 3B-3C in particular show CFZ induces megakaryocytic surface markers CD61 (early) and CD41 (late) in K562 cells. K562 cells were treated as indicated for 72 h (Phorbol myristate acetate (PMA) was used as positive control) and then were stained with IgG isotype control or CD61 (B) & CD41 (C) IgG antibodies and were analyzed by flowcytometry (n=3). ***p<0.0001. PMA was used as a positive control.

FIG. 3D-3E in particular show CFZ induces megakaryocytic surface markers CD61 and CD41 in CP-CML cells. CD61 (D) and CD41 (E) surface expression in CP-CML (gated monocytes) cells after treatment with 2.5 µM CFZ for 72 h were assessed by flowcytometry. *p<0.05, ***p<0.0001.

FIG. 4A-4C show CFZ shows cytotoxic synergy with imatinib and dasatinib. CFZ reduces K562 viability synergistically with imatinib (IMT) and dasatinib. K562 cells were treated as indicated for 48 h and cell viability was determined by CellTiter-Glo luminescent cell viability assay (A) graphical representation of mean±SEM of three independent experiments. (B&C) Compusyn analysis of synergism, combination index (CI) value 1<represents synergy.

FIG. 7A-7C show CFZ increases bioavailability of imatinib in rat. Assessment of pharmacokinetic properties of imatinib and CFZ alone or in combination in SD rats (n=6).

DETAILED DESCRIPTION

Figure 1A:
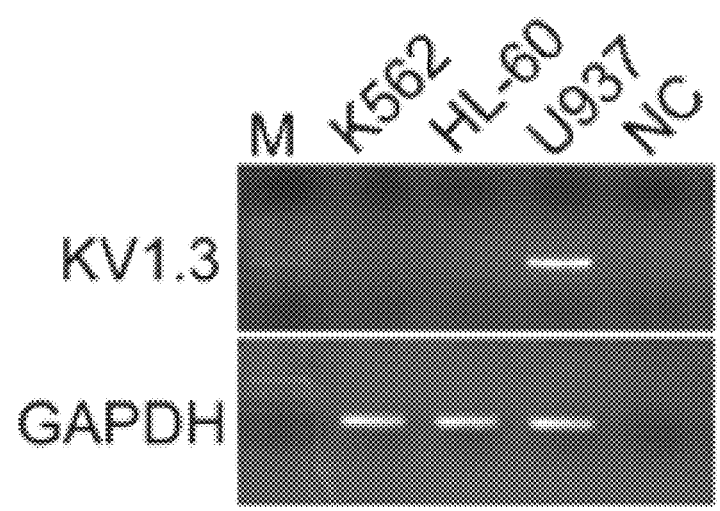
FIGS. 1A-1I show CFZ induces apoptosis in K562 and chronic phase CML patient-derived mononuclear cells (CP-CML cells), with particular efficacy against CP-CML cells from imatinib-resistant patients.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Here the investigators have invented CFZ as an anti-CML agent in cells lacking KV1.3 (Leanza, et al.; EMBO Mol Med; (4); 577-593; 2012, Smith, et al.; J Biol Chem; (277); 18528-18534; 2002), and show that CFZ exerts its anti-CML effects by inducing apoptosis in CML cells and leukemia stem cells. Further, CFZ has been shown here to induce differentiation in CML cells at sub-lethal concentration. Further, CFZ is shown here to synergize with imatinib and dasatinib and combination of CFZ with imatinib almost obliterates quiescent leukemia stem cells. Furthermore, it has also been shown here that CFZ increases the bioavailability of imatinib by 109%.

Experimental Methods

Culture of Cell Lines

Human K562 (CCL-243) CML, AML cell lines HL-60 (CCL-240), U937 (CRL-1593.2), and HEK-293T (CRL-3216) were from the American Type Culture Collection (ATCC; Manassas, Va.). Cells were maintained as per ATCC instructions in RPMI-1640 medium (Invitrogen, Thermo-Fisher Scientific, Carlsbad, Calif.) supplemented with 10% fetal bovine serum (Invitrogen) and 1× antibiotic-antimycotic (Invitrogen) solution.

Culture of Primary Cells Isolated from CML Patients or Healthy Donors

Peripheral blood samples were obtained from chronic phase (CP-CML), accelerated phase (AP) or blast crisis (BC) CML patients (BCR– ABL+ v e freshly diagnosed, Imatinib-resistant or responders), and healthy donors from King George's Medical University (Clinical Hematology and Medical Oncology division), Lucknow, following ethical approval (Approval No: 1638/R. Cell-12) as per institutional ethical guidelines after written consent. Peripheral blood mononuclear cells (PBMC) were isolated on Percoll (Sigma) density gradient by centrifugation. Briefly, the blood was collected in vials coated with trisodium citrate buffer. Cells were then centrifuged 700 g for 10 min and plasma was removed. The pellet was resuspended in 6 ml Hank's balanced salt solution (HBSS; Invitrogen, Thermo Fisher Scientific), and then 2 ml of 6% Dextran in HBSS was added to it. Cells were then incubated at 37° C. for 30 min. The supernatant was then collected and centrifuged at 300 g for 5 min. The pellet was then resuspended in 2 ml HBSS supplemented with 0.18% glucose and loaded onto percoll gradient. PBMCs were then isolated by centrifugation.

RNA extraction and Reverse Transcription-PCR to determine KV1.3 expression in cell-lines and CD34+ CP-CML cells.

Total RNA was extracted using TRI Reagent (Life Technologies, Carlsbad, Calif.) according to manufacturer's instructions. Total RNA (2 µg) was reverse transcribed using High-Capacity cDNA Reverse Transcription Kit (Applied Biosystems; Foster City, Calif.). For KV1.3, cDNAs was amplified using the following primers: oligonucleotide sequences (5'-3') are: KV1.3-F-TGGTTCTCCTTCGAACT-GCT, KV1.3-R CAATGCGATGGTCAAGACAC. For GAPDH following pair of primers were used; GAPDH-F-GCAGGGGGGAGCCAAAAGGGT, GAPDH-R-TGGGTGGCAGTGATGGCATGG. The PCR conditions were as follows. Initial denaturation at 94° C. for 2 min, followed by 25 cycles at 94° C. for 1 min, 56° C. for 1 min and 72° C. for 1 min), followed by 10 min at 72° C. PCR products were resolved by 1.5% agarose gel electrophoresis.

Figure 1B:
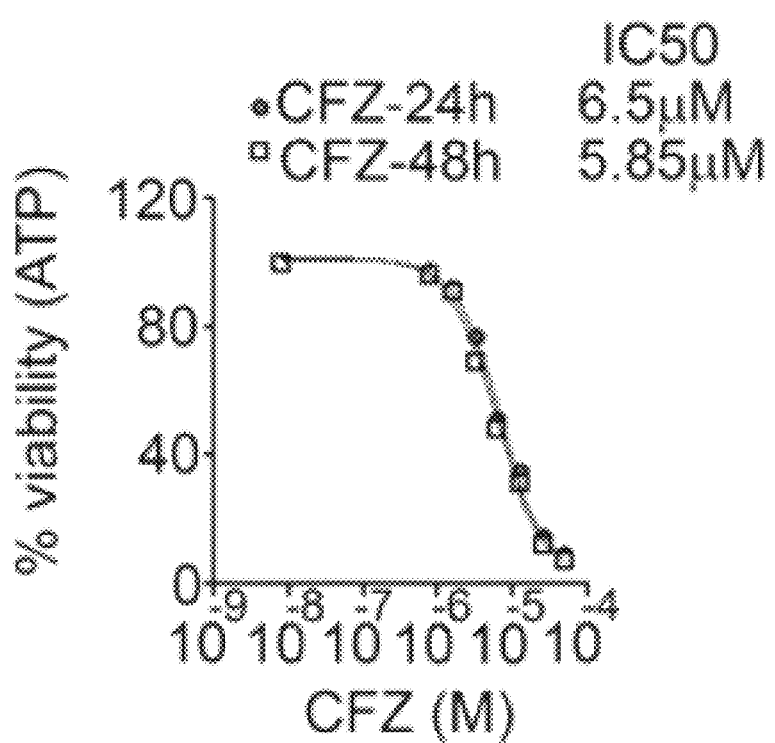

Determination of CFZ's Effect on Cell Viability and Apoptosis a. CellTitre-Glo assay: Cell viability (in FIG. 1B, FIG. 4 and FIG. 6A) assays was performed using the ATP-based CellTiter-Glo Luminescent cell viability assay (Promega Madison, Wis.) as per the manufacturer's instruction. Briefly, ($1.25 \times 10^5$) K562 cells/ml (FIG. 1B and FIG. 4) or CD34+ cells from healthy donors (FIG. 6A) were cultured in 48-well plates and were treated as indicated in the respective figures and figure descriptions (vehicle; V=0.1% DMSO). Cells were then incubated with CellTitre-Glo reagent for 15 min. Luminescence was recorded in a GloMax-96 Microplate luminometer (Promega, Madison, Wis.) with an integration time of 1 s per well.

b. Analysis of apoptosis by Annexin V staining and flow cytometry

Figure 1C:
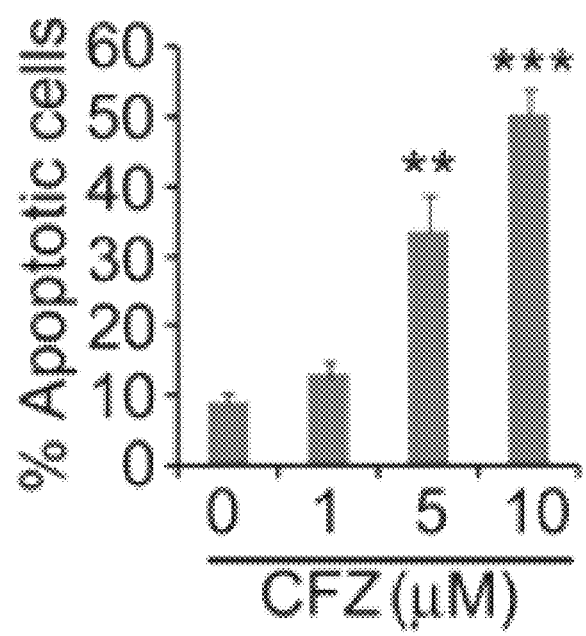
Figure 1D:
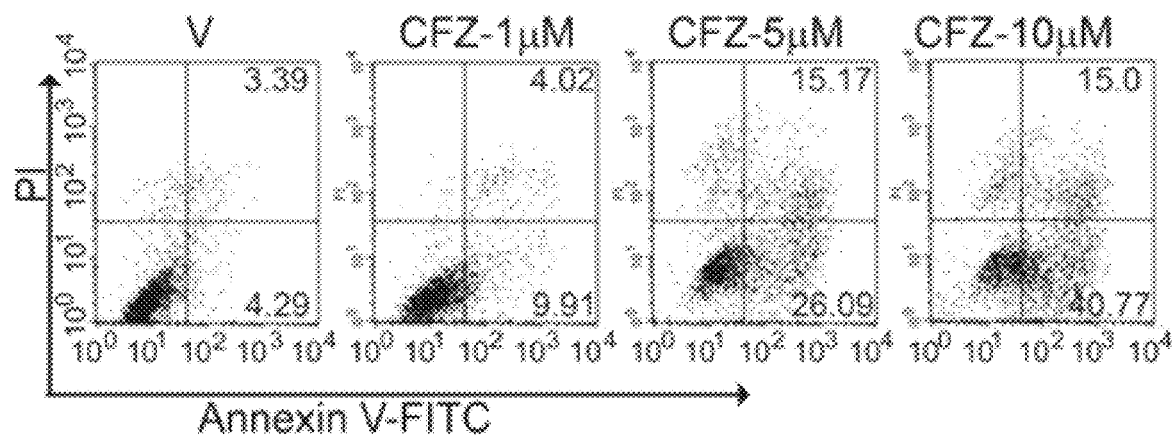
Figure 1E:
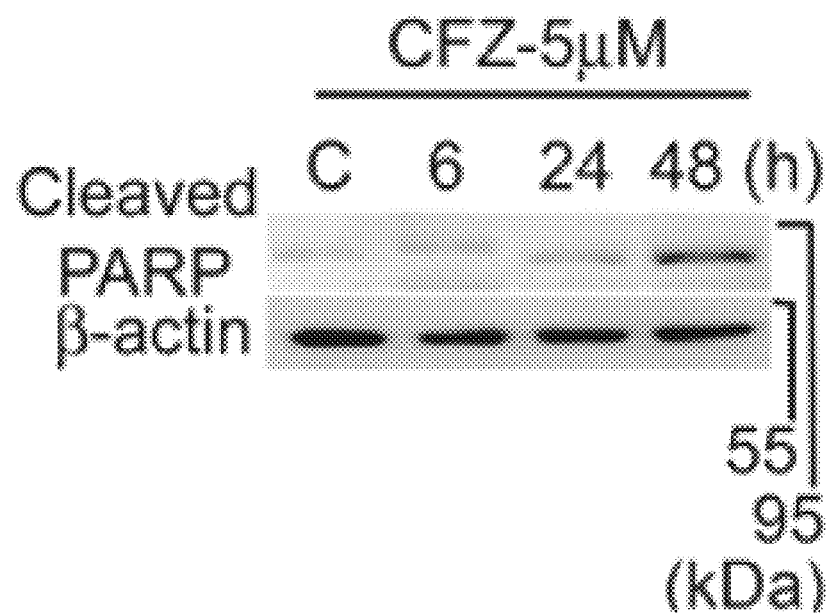

K562 (FIG. 1C-D) and primary CP-CML cells (FIG. 1H-I) were cultured in 6 well plates ($2 \times 10^5$ cells/well) and were treated with indicated concentrations of compounds as described in respective figures and their descriptions. Cells were then harvested and washed, and incubated in binding buffer (Annexin V Binding Buffer, BD Pharmingen) with 0.3% Annexin V-FITC and PI for 15 min at room temperature in dark. Apoptosis was measured by FACSCalibur flow cytometer (Becton Dickenson, San Jose, Calif.).

c. TUNEL assay

Figure 1F:
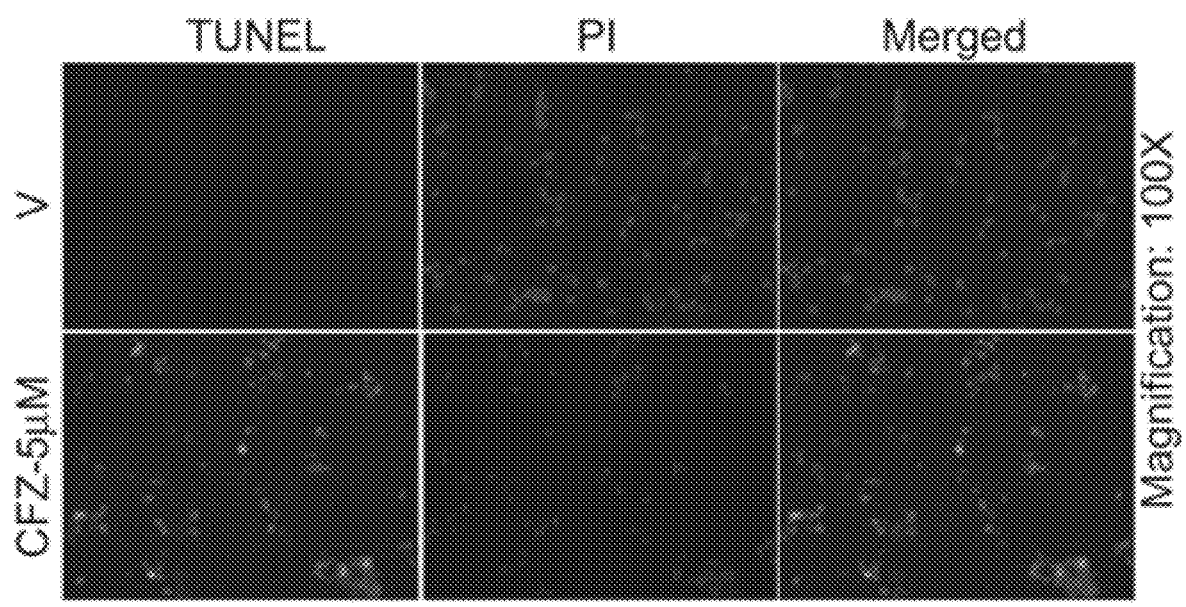

Pro-apoptotic potential was analysed using a Fluorometric APO-BrdU™ TUNEL Assay Kit (Invitrogen) according to the manufacturer's protocol (FIG. 1F). Cells were treated with Vehicle (0.1% DMSO) or CFZ (5 µM) for 48 h. Cells were then fixed in formaldehyde (4%) for 25 min at 4° C., permeabilized with 0.2% Triton-X100 and washed with PBS. Cells were then incubated in Terminal Deoxynucleotidyl Transferase (TdT) reaction buffer without TdT enzyme for 7 minutes at room temperature and then in TdT buffer with TdT enzyme at 37° C. in dark. After termination of TdT reaction, cells were stained with 5 µg/ml of PI for 15 min in dark followed by washing and analysed with fluorescence microscopy.

Western Blotting to Determine CFZ-Mediated Regulation of Protein Expressions:

K562 cells were cultured in 6 well plates and treated as indicated in figures or descriptions of FIG. 1E, FIG. 1G and FIG. 2D-E. Cells were then homogenized in lysis buffer containing 50 mM Tris-HCl, pH 7.5, 150 mM NaCl, 1% NP40, 5 mM EDTA, 1 mM DTT, protease and phosphatase inhibitor cocktails (Sigma) and incubated on ice for 30 min followed by 5 cycles of freeze-thaw. Samples were then centrifuged at 14000 rpm at 4° C. for 30 min. Supernatants were then quantified by Bichinchonic acid (Sigma)-based protein estimation. Equal amount of proteins were solubilized in Laemmli buffer, and were resolved by 10%-12% SDS PAGE and transferred onto PVDF membranes (Millipore; Billerica, Mass.). Membranes were blocked in 5% (w/v) non-fat dried milk powder (Sigma) in PBS containing 0.2% Tween 20 (Sigma). The membranes were then sequentially incubated with primary and secondary antibodies in PBS containing 0.2% Tween 20 and 2.5% BSA (with 3 washes in between). Immunoreactivity was detected using a chemiluminescent HRP Substrate (Millipore) in a LAS 4010

Chemi-doc Imager (GE Healthcare, Little Chalfont, UK). Antibodies used: phospho-STAT5, STAT5, cleaved PARP and caspases-3, -8, -9, pCrkL, Bcl2 and Bax antibodies were from Cell Signaling Technology (Boston, Mass.). Mouse monoclonal anti-β-Actin-Peroxidase and horse raddish peroxidase-conjugated secondary antibodies were from Sigma-Aldrich. For immunoblotting all primary antibodies were used in 1:1000 dilutions except β-actin (1:50000). Secondary antibodies were used at 1:10000 dilutions.

CD34+ Cells Isolation and Analysis of Apoptosis

Cells from imatinib-resistant patients (FIG. 2A-B, 2F and FIG. 5) or healthy volunteers (FIG. 6) were first selected with anti-CD34 magnetic beads in a magnetic-activated cell sorter system using EasySep™ Human CD34 Positive Selection Kit (STEMCELL Technologies, Vancouver, Canada) according to manufacturer's instructions. Cells were then cultured in IMDM (StemSpan SFM II) supplemented with 5 growth factor-Flt3L, SCF, IL-3, IL-6 and TPO (StemSpan CD34+ Expansion Supplement). Isolated cells were then labeled with CD34-PE antibody (BD) and CD34+ purity was determined in a FACSAria flow cytometer (Becton Dickenson, San Jose, Calif.). The observed purity was 80-90%.

Figure 2A:
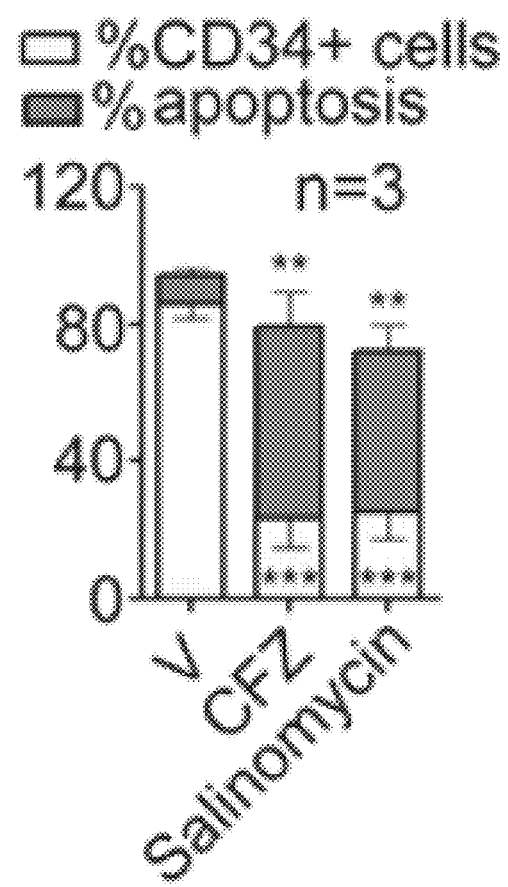
FIGS. 2A-2G show CFZ reduces leukemia stem cell (LSC) population by inducing apoptosis and suppresses the expression of genes that are important for LSC maintenance.

For assessing apoptosis in the CD34+ population from CML patients, these cells were then treated as indicated in the figures and figure descriptions (FIG. 2A). At the end of treatment, cells from each treatment group were divided in two separate tubes. One group was stained with CD34-PE and the other group was stained with Annexin V FITC/PI antibodies. The CD34+ cell count and extent of apoptosis were determined in a FACSAria flow cytometer.

Figure 6A:
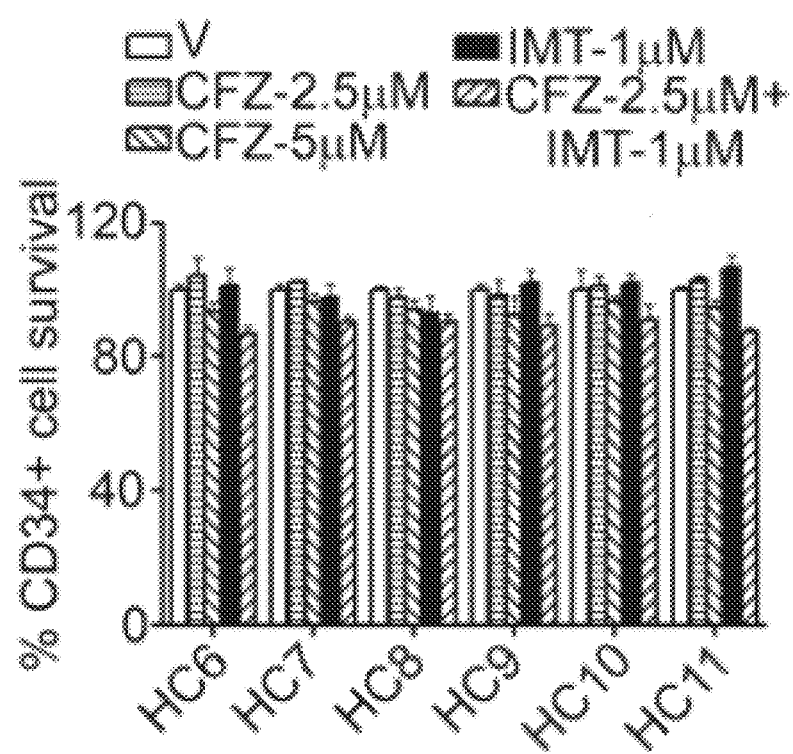
FIG. 6A-6B show CFZ alone or in combination with imatinib does not affect viability in CD34+ cells from healthy donors. CFZ does not reduce viability of CD34+ cells from healthy donors. A. CD34+ cells were isolated from healthy donors (HC; individual donors are indicated as HC6 and so forth) and were treated as indicated for 48 h. Cell viability was assessed by CellTiter-Glo luminescent cell viability assay. B. CD34+ cells (top panel indicates purity of CD34+ cells) from HC11 were treated as indicated and apoptosis was evaluated by Annexin V staining.
Figure 6B:
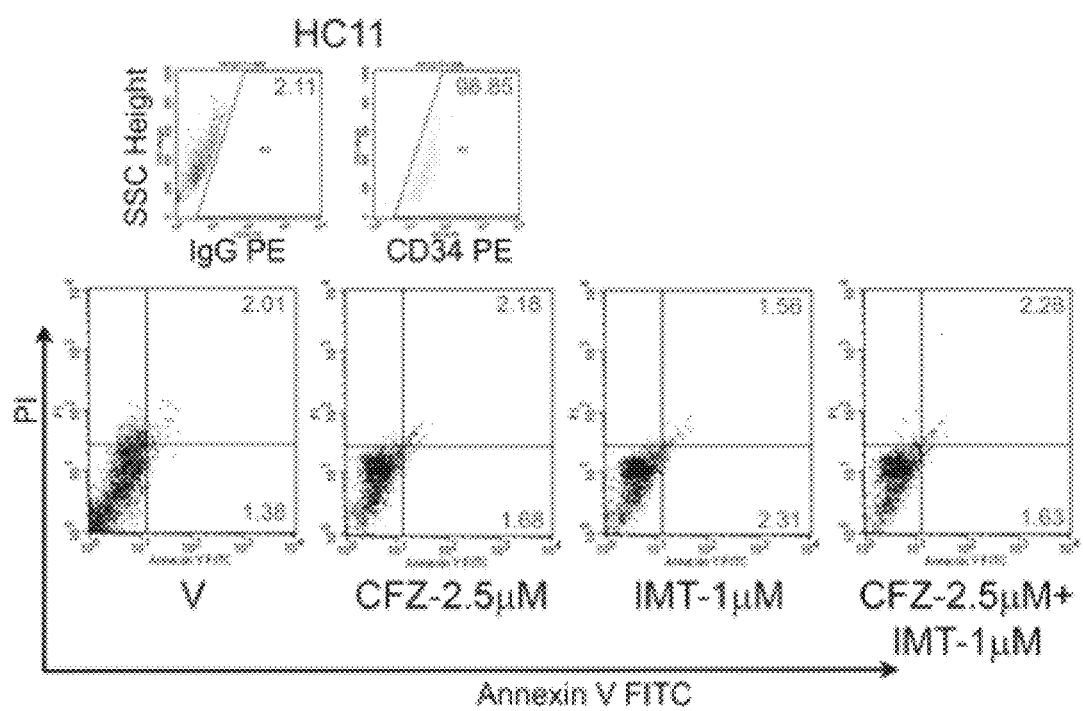

For assessing viability or apoptosis in the CD34+ population from healthy donors, cells were treated as indicated in the figures or figure descriptions (FIG. 6A-B). At the end of treatment, cells viability was determined by CellTiter-Glo Luminescent cell viability assay as described in Example 4 or apoptosis was determined by staining with Annexin V FITC/PI antibodies and extent of apoptosis were determined in a FACSAria flow cytometer.

For assessing apoptosis in CD34+ CD38+ and CD34+ CD38− subpopulations from CML patients, CD34+ cells were isolated as above and were treated with V or 2.5 µM CFZ for 96 h and then stained with PE-conjugated anti-CD34, FITC-conjugated anti-CD38 antibodies for 30 min and then stained with Annexin V-APC/PI at room temperature for 15 minutes and then were gated into CD34+38+ and CD34+38− populations and apoptosis was assessed in a FACSAria flow cytometer.

Aldeflour assay to determine CFZ's effect on aldehyde dehydrogenase activity in CP-CML cells.

Figure 2B:
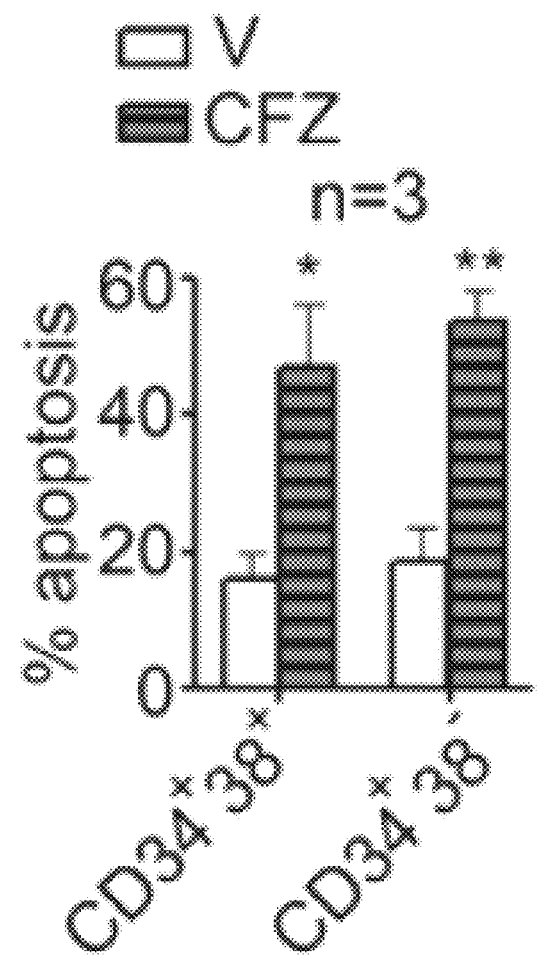
Figure 2C:
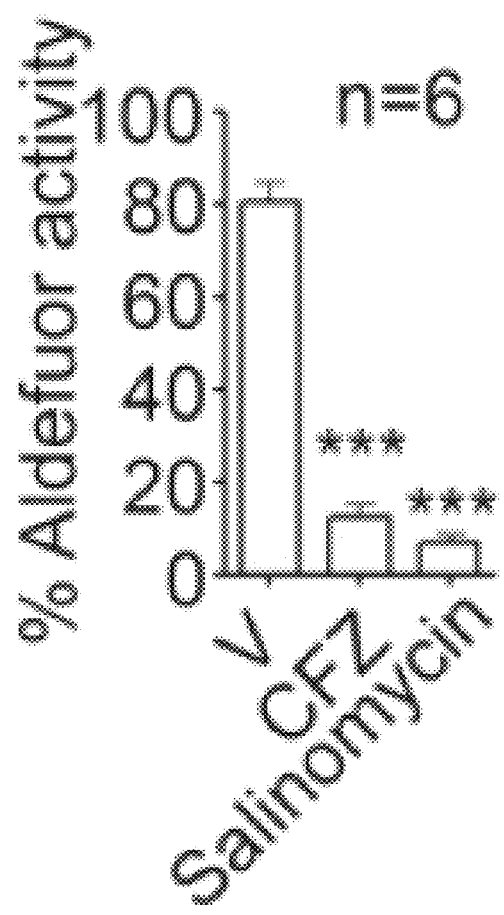
Figure 2D:
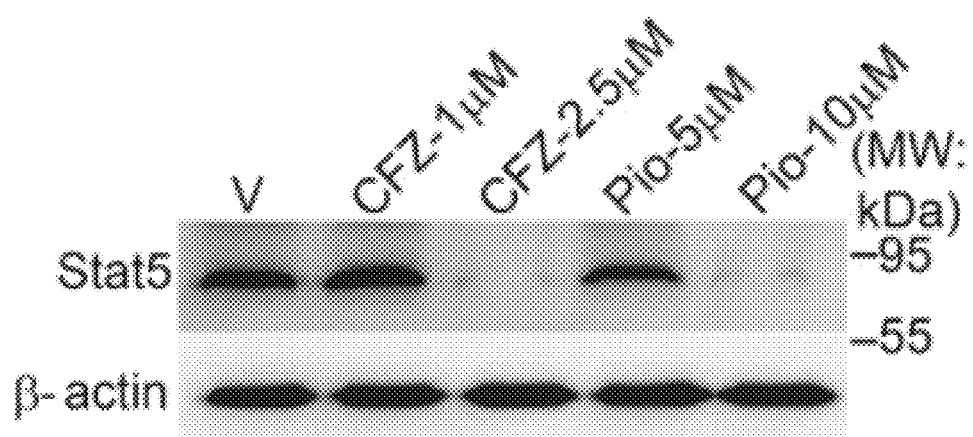

CP-CML cells isolated from imatinib-resistant patients were treated with vehicle (V; 0.1% DMSO), CFZ or salinomycin (both 5 µM) for 48 h (FIG. 2C). Aldehyde dehydrogenase activity in CP-CML cells was assessed using an Aldefluor kit (STEMCELL technologies) by flow cytometry (FACSCalibur).

Quantitative real-time PCR (QRT-PCR)-based evaluation of stem cell factors in CD34+ CML cells.

Figure 2E:
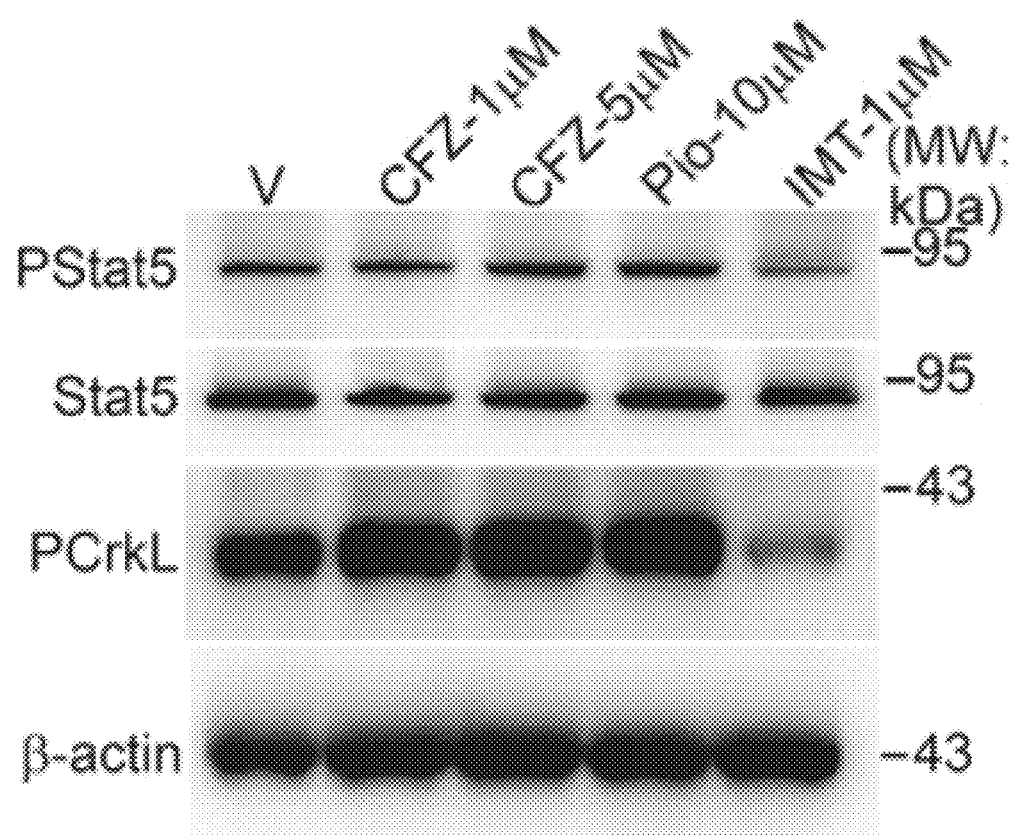
Figure 2F:
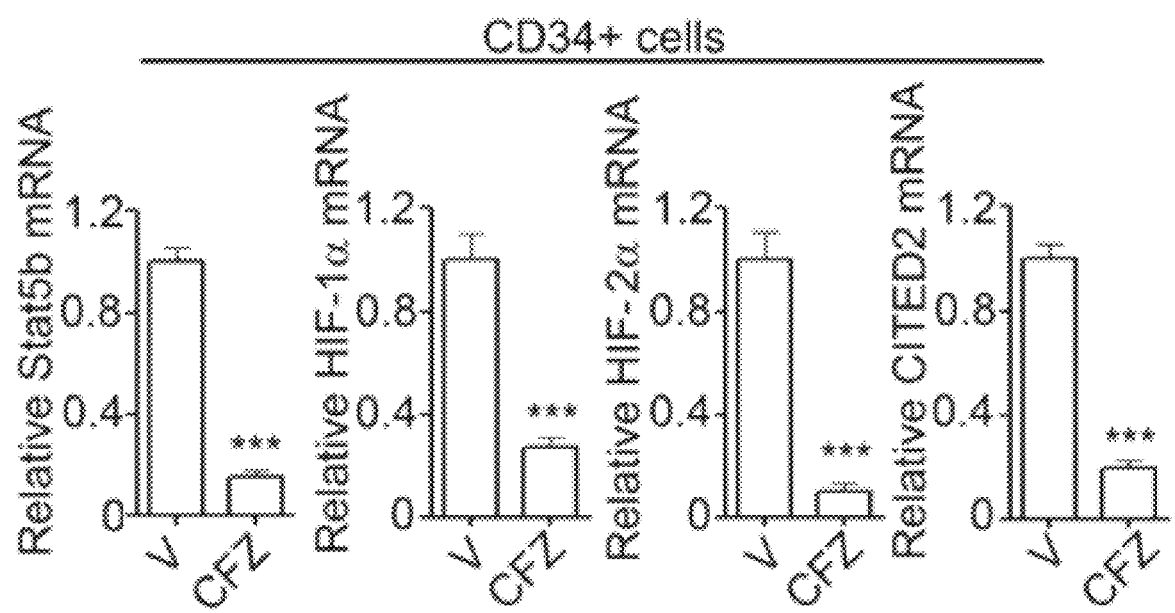

CD34+ cells were isolated from imatinib-resistant CP-CML cells as described above. Cells were then treated with vehicle (V; 0.1% DMSO) or CFZ (5 µM) for 24 h. Total RNA was isolated from CD34+ cells as described above, using TRI reagent. 2 µg total RNA was reverse transcribed using High-Capacity cDNA Reverse Transcription Kit (Applied Biosystems; Foster City, Calif.). Quantitative real-time PCRs (QRT-PCR) were performed on a LightCycler 480 System (Roche, Indianapolis, Ind.) using VeriQuest SYBR Green qPCR Master Mix (Affymetrix, Thermo Scientific). The QRT-PCR primers were designed using Universal ProbeLibrary Assay Design Center (Roche Life Science). Primer sequences (5'-3') hSTAT5B-For-TGAAG GCCAC-CATCATCAG, hSTAT5B-Rev TGTTCAAGATCTCGCC ACTG, hHIF-1α-For-TTTTTCAAGCAGTAGGAAT-TGGA, hHIF-1α-Rev-GTGATGTAGT AGCTGCAT-GATCG, hHIF-2α-For-GACAGAATCACAGAACTGAT-TGGT, hHIF-2α-Rev-CGCATGGTAGA ATTCATAGGC, hCITED-2-For-TCACTTTCAAGTTGGCTGTCC, hCITED-2-Rev-CATTCCACACCCTATTATCATCTGT. The data were analyzed by ΔΔCT method with GAPDH (GAPDH-For-AGCCACATCGCTCAGACAC, GAPDH-Rev-GCC CAATACGACCAAATCC) used as an internal control (FIG. 2F).

Analysis of Differentiation in Response to Sub-Lethal Concentrations of CFZ.

Figure 3A:
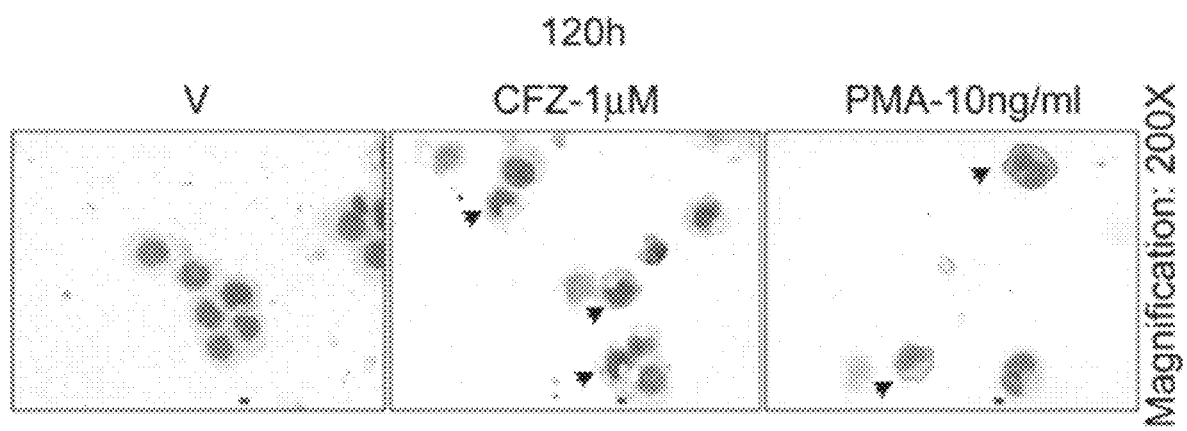
FIGS. 3A-3E show CFZ at sub-lethal concentration induces megakaryocytic differentiation in K562 and CP-CML cells.

May-Grünwald Giemsa Staining: To assess the changes in nuclear morphology, cells treated with vehicle (0.1% DMSO), CFZ (indicated concentrations in FIG. 3A) or PMA (positive control; 10 ng/ml) for 120 h (FIG. 3A). Cells were then washed with phosphate buffer saline (PBS) and were attached to glass slides by cytospin. These slides were stained with Giemsa and May-Grünwald solution (Sigma) as per manufacturer's instruction. Cells were then visualized by microscopy.

Figure 3B:
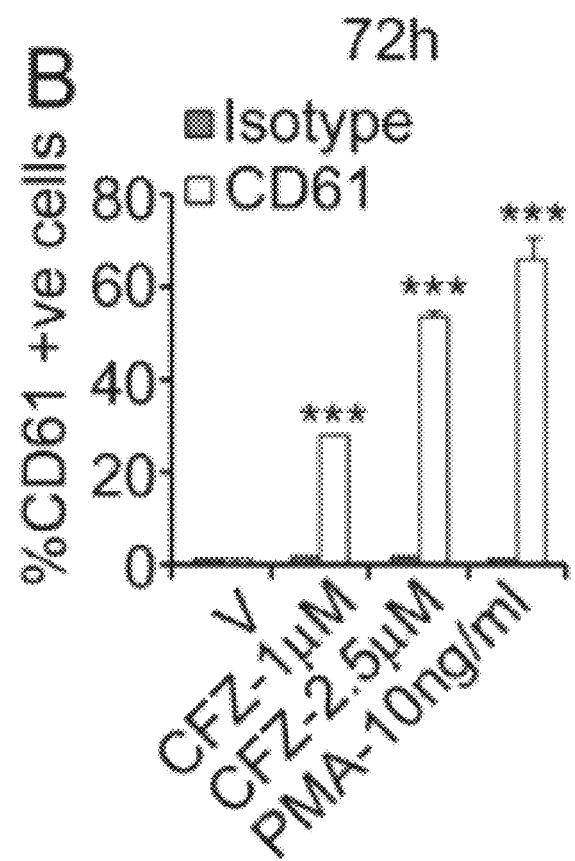
Figure 3C:
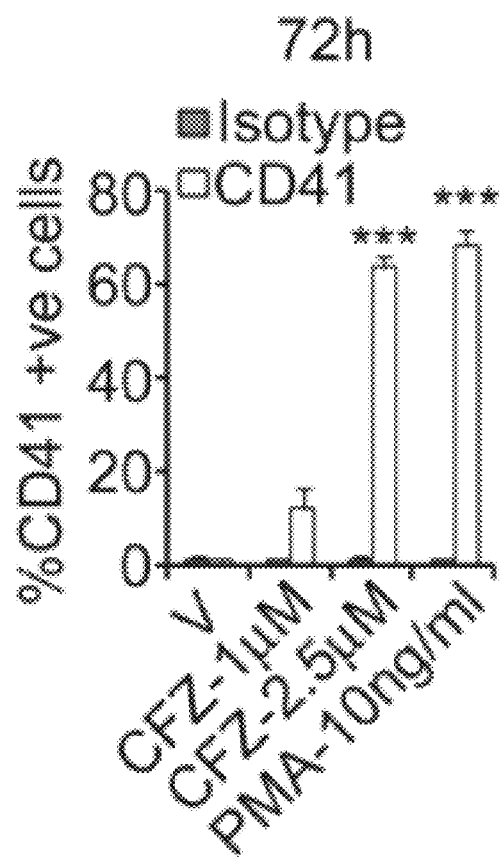

Differentiation analyses by flow cytometry: K562 (FIG. 3B-C) or primary CP-CML cells (FIG. 3D-E) were treated with vehicle, CFZ and PMA as indicated in the respective figures and figure descriptions for 72 hrs. Cells were then harvested, washed, and centrifuged, resuspended in 100 µl PBS and were stained with CD41-FITC or CD61-PE antibodies for 30 min at room temperature (in dark). After incubation, the cells were washed and resuspended in 300 µl PBS and were analyzed on a FACSCalibur flow cytometer.

Determination of CFZ's Effect on Apoptosis in Quiescent LSCs; CFSE Assay.

For assessing apoptosis in quiescent LSCs, purified CD34+ cells were first stained with carboxyfluorescein succinimidyl ester (CFSE; Invitrogen) for 30 min. Cells were then washed and resuspended in SFM medium with 5 growth factors and were kept at 37° C. overnight. Next day, cells were treated as indicated in SFM medium with growth factors and were maintained further for 4 days with supplementation of the drugs every 48 h (drug concentrations in FIG. 5 and its description). Cells were then harvested, washed, and were labeled with CD34-PE and Annexin-APC antibodies and then gated into non-dividing cells (CD34+ CFSE$^{bright}$) and dividing cell (CD34+CFSE$^{dim}$) population based on CFSE fluorescence intensity. Cells cultured in the presence of colchicine (100 ng/ml; Sigma) were used to assess the range of CFSE fluorescence exhibited by cells that were undivided at the end of the culture time by using a FACSAria flow cytometer. Number of cells or apoptosis was determined by flowcytometry.

Pharmacokinetics of CFZ and IMT Alone or in Combination.

Figure 7A:
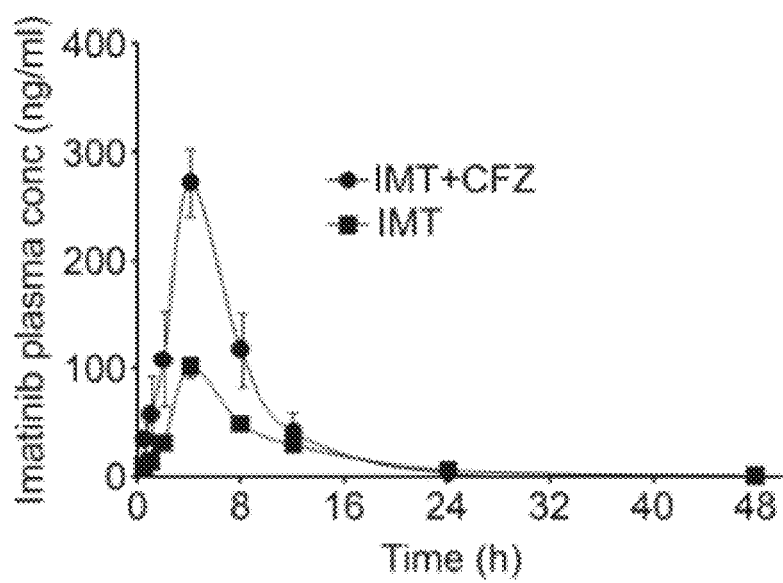
Figure 7B:
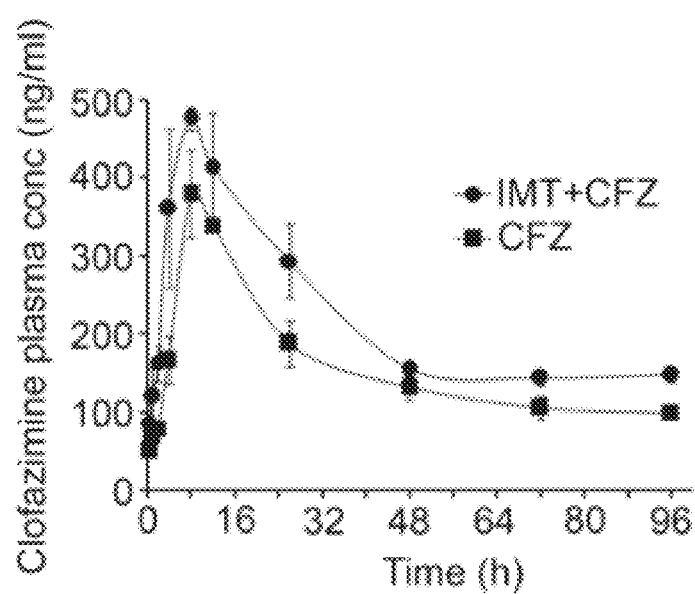

Sprague-Dawley rats (n=6 per group) were divided into 3 groups. The imatinib group (46.66 mg/kg imatinib mesylate; equivalent to human dose of 400 mg), the CFZ group (11.66 mg/kg CFZ; equivalent to human dose of 100 mg CFZ) and the combination group (IMT; 46.66 mg/kg and CFZ; 11.66 mg/kg) were orally administered indicated drugs following overnight fasting and blood samples were collected at 0.5, 1, 2, 4, 8, 12, 24, 48, 72, 96 and 120 hours (FIG. 7). Plasma was separated and processed for analysis by LC-MS/MS. For pharmacokinetic and statistical analysis, plasma concentration versus time data were plotted and analyzed by non-compartmental analysis method using WinNonlin (Pharsight, Mountain View, Calif.) software.

Statistical Analysis

All data are expressed as mean±SEM of three independent experiments unless otherwise indicated. Statistical analyses were performed using GraphPad Prism 5.0. Comparison between two groups was assessed by unpaired two-tailed Student's t-test or Mann-Whitney test. Equality of variances was tested by F-test. Statistical analyses involving >2 groups were performed by one way or two way ANOVA followed by Bonferroni's post-test or Kruskal-Wallis test followed by Dunn's test. For intra sample variances Levene's median test (equal sample size; using XLSTAT) or Bartlett's test (unequal sample size) was performed. $P<0.05$ was accepted as statistically significant.

EXAMPLES

The following examples are given by way of the illustration of the present invention and should not be construed to limit the scope of the present invention.

Example 1. CFZ Induces Apoptosis in K562 and CP-CML Cells

Figure 1G:
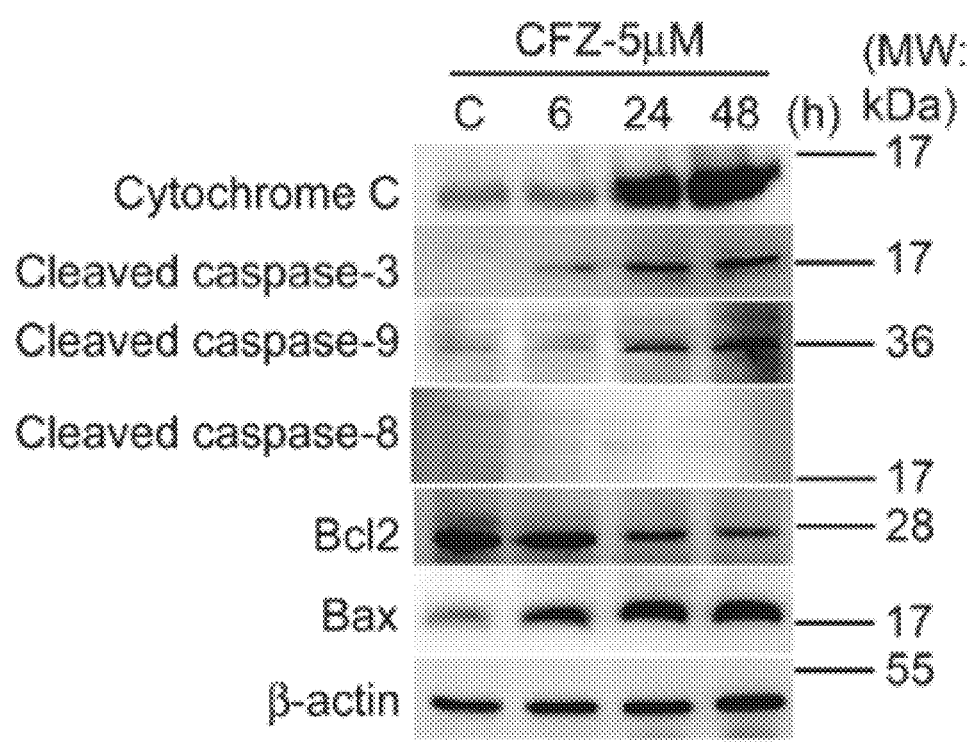
Figure 1H:
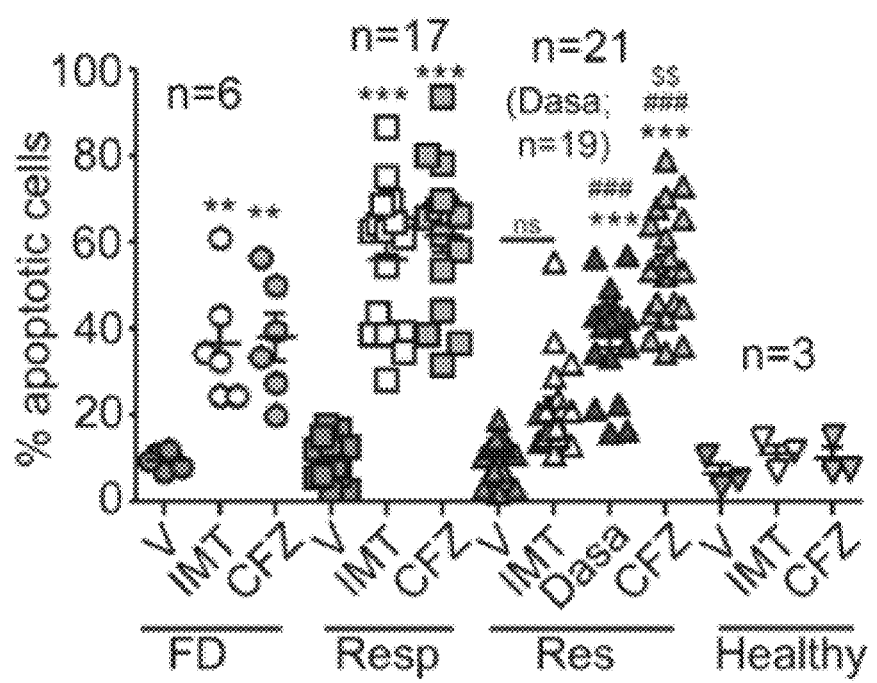
Figure 1I:
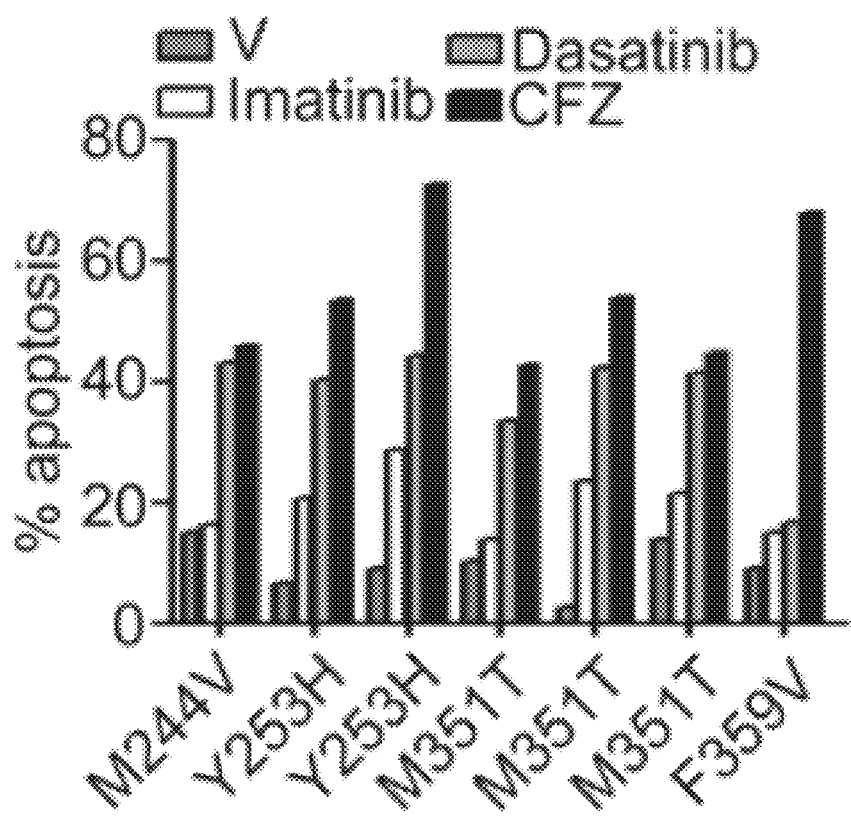

In K562 CML cell-line that does not express KV1.3 [(Leanza, et al.; EMBO Mol Med; (4); 577-593; 2012, Smith, et al.; J Biol Chem; (277); 18528-18534; 2002) FIG. 1A], we found CFZ to reduce viability with a pharmacologically relevant $IC_{50}$ (48 h) concentration of 5.85 μM (FIG. 1B) [human plasma $C_{max}$ of CFZ is 0.4-4 mg/L; equivalent to 0.84 μM-8.4 μM (Cholo, Steel, Fourie, Germishuizen and Anderson; J Antimicrob Chemother; (67); 290-298; 2012, Schaad-Lanyi, et al.; Int J Lepr Other Mycobact Dis; (55); 9-15; 1987, Yawalkar, et al.; Lepr Rev; (50); 135-144; 1979, O'Connor, et al.; Drug Metab Rev; (27); 591-614; 1995)]. The loss of viability was due to apoptosis as observed by Annexin V staining (FIG. 1C-D), poly (ADP-ribose) polymerase (PARP) cleavage (FIG. 1E) and terminal deoxynucleotidyl transferase dUTP nick end labeling (TUNEL) (FIG. 1F). CFZ induced cytochrome C release and activated caspase-3 and -9 but not -8 (FIG. 1G), suggesting mitochondria-mediated apoptosis which was consistent with decreased B-cell lymphoma 2 (Bcl-2) and increased Bax (also known as Bcl-2-like protein 4) expression (FIG. 1G). CFZ also induced apoptosis in peripheral blood mononuclear cells from chronic phase CML patients (CP-CML cells) with an efficacy that was comparable to imatinib in cells from freshly diagnosed and imatinib responders but was higher than imatinib and dasatinib in imatinib-resistant cells, while it didn't affect cells from control donors (FIG. 1H). Among the CP-CML cells harboring BCR-ABL mutations, CFZ showed comparable (for M244V) or higher (Y253H, M351T and F359V) efficacy than dasatinib (FIG. 1I). These results indicate that CFZ induces cell death by apoptosis in K562 leukemia cell line as well as primary CML cells obtained from CML patients and further indicate that CFZ shows higher efficacy than imatinib and dasatinib in killing CML cells from imatinib-resistant patients.

Example 2. CFZ Reduces LSC Population by Inducing Apoptosis in these Cells and Downregulates Factors that are Important for LSC Maintenance and Function CFZ induced apoptosis in CD34+ LSC population isolated from imatinib-resistant CP-CML patients (n=3, FIG. 2A).

Figure 2G:
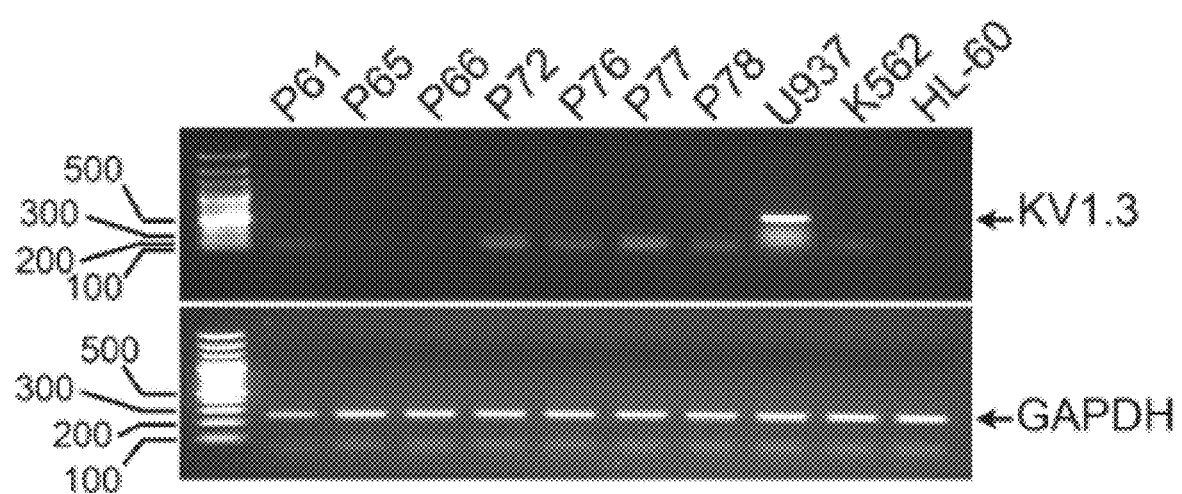

Detailed evaluation revealed that CFZ induced apoptosis both in committed CD34+38+ and primitive CD34+38− progenitor cells (n=3, FIG. 2B). Increased aldehyde dehydrogenase (ALDH) activity is another hallmark of cancer stem cells (Marcato, et al.; Cell Cycle; (10); 1378-1384; 2011) and CFZ remarkably decreased it in imatinib-resistant CP-CML cells (n=6, FIG. 2C). Stat5 activation is responsible for disease progression, drug resistance as well as LSC maintenance in CML and CFZ suppressed stat5 protein (FIG. 2D) and mRNA (FIG. 2F) expressions without altering its phosphorylation in K562 cells (FIG. 2E). Further, CFZ also reduced stat5b, HIF-1α, HIF-2α and CITED2; the master regulator of LSC quiescence (Prost, et al.; Nature; (525); 380-383; 2015), transcripts in CD34+ cells isolated from imatinib-resistant patients (FIG. 2F). CrkL is a substrate of BCR-ABL tyrosine kinase which activates it by directly phosphorylating at Tyr207. CFZ did not alter CrkL phosphorylation (FIG. 2E) indicating that it's not a BCR-ABL inhibitor per se, while BCR-ABL inhibitor imatinib successfully inhibited its phosphorylation (FIG. 2E). The anti-LSC effects of CFZ was not KV1.3-dependent as CD34+ cells from imatinib-resistant patients did not express KV1.3 (FIG. 2G)

Figure 3D:
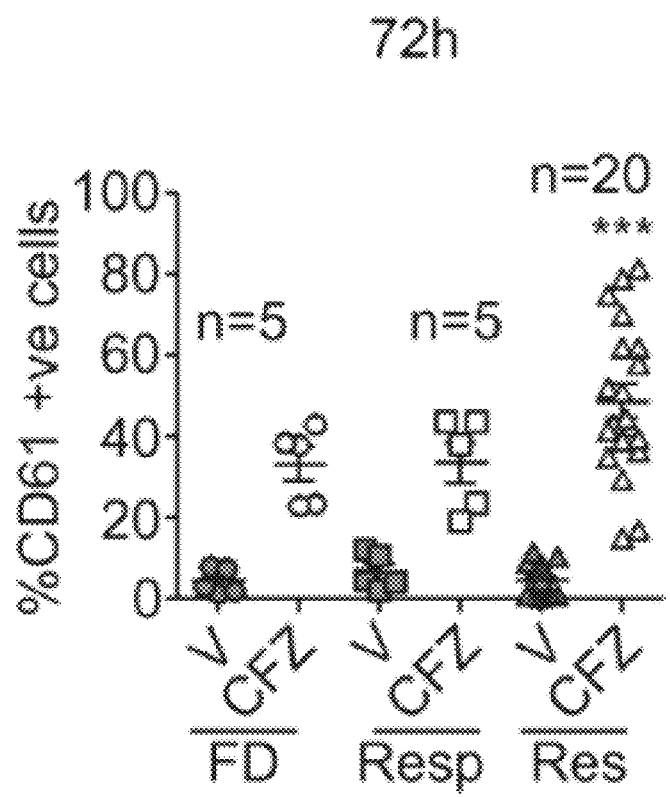
Figure 3E:
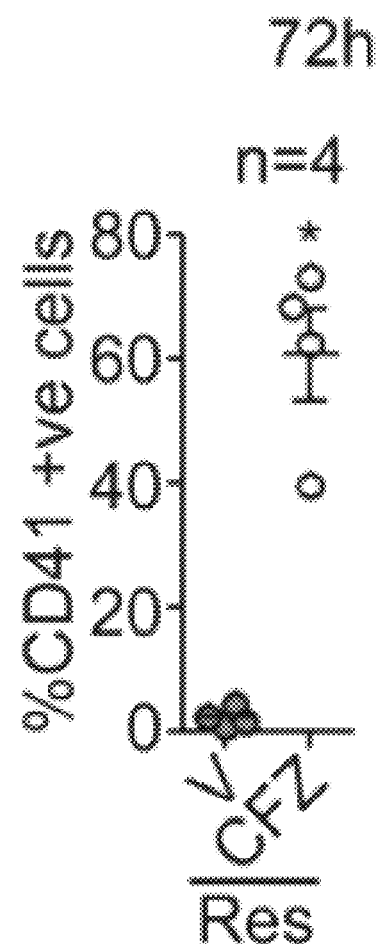

Example 3. CFZ Induces Megakaryocytic Differentiation in K562 and CP-CML Cells CFZ at sub-lethal concentration (1 μM; 120 h) induced megakaryocytic differentiation phenotype in K562 cells characterized by increased cellular size, nuclear to cytoplasmic ratio and lobulated nuclei as visualized by May-Grünwald-Giemsa staining (FIG. 3A). CFZ also increased megakaryocytic surface markers (CD61 and CD41) in K562 (FIG. 3B-C) and CP-CML cells (FIG. 3D-E).

Example 4. CFZ Synergizes with Imatinib and Inhibits CML Cells

Figure 4A:
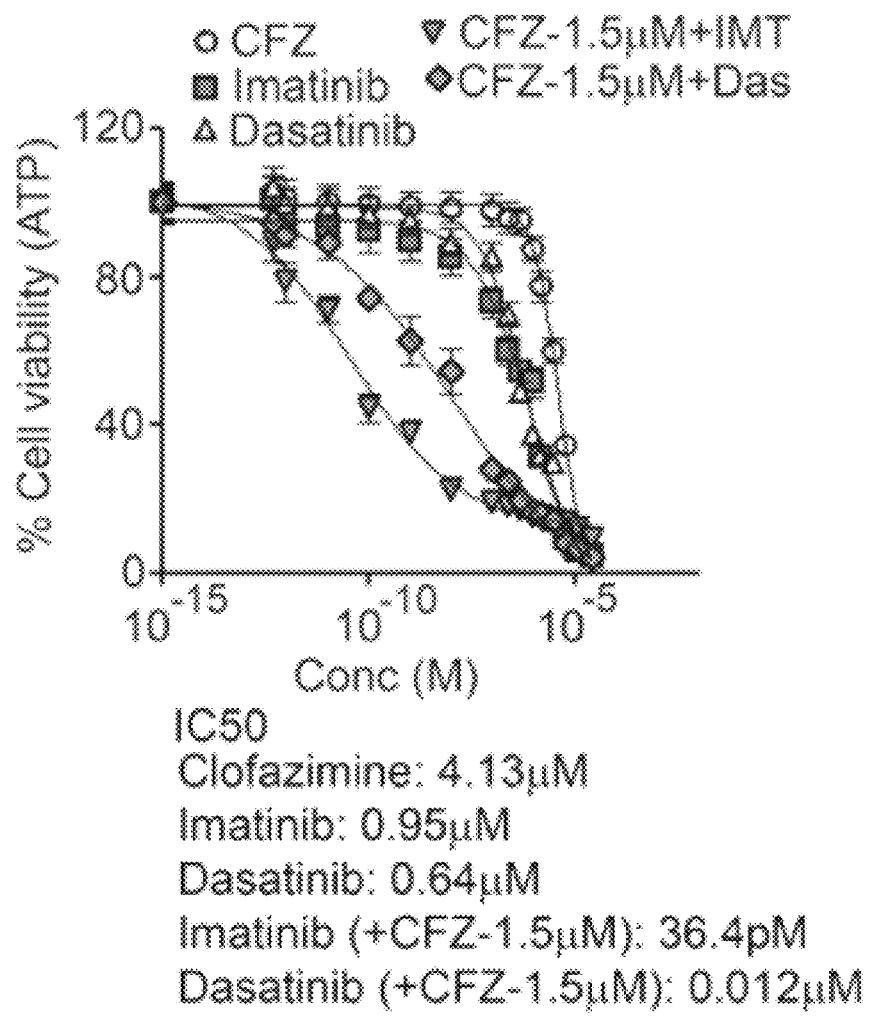

We next assessed if CFZ synergizes with imatinib. In a K562 cell viability assay (48 h) imatinib, dasatinib and CFZ displayed $IC_{50}$s of 0.95 μM, 0.64 μM and 4.13 μM respectively. However, combining 1.56 μM CFZ, [which is close to the average human plasma level of CFZ (0.7 mg/L) following daily oral administration of 100 mg CFZ (Cholo, Steel, Fourie, Germishuizen and Anderson; J Antimicrob Chemother; (67); 290-298; 2012)] with imatinib reduced the $IC_{50}$ of imatinib to 36.4 μM (FIG. 4A). The combination index (CI) calculated using the Compusyn program revealed CI values <1 (FIG. 4B), indicating synergistic effect. CFZ also displayed synergism with dasatinib, where dasatinib's $IC_{50}$ of 0.64 μM (alone) was reduced to 0.0124 μM in presence of 1.56 M CFZ (FIG. 4A) and the calculated CI values were <1 (FIG. 4C).

Figure 5A:
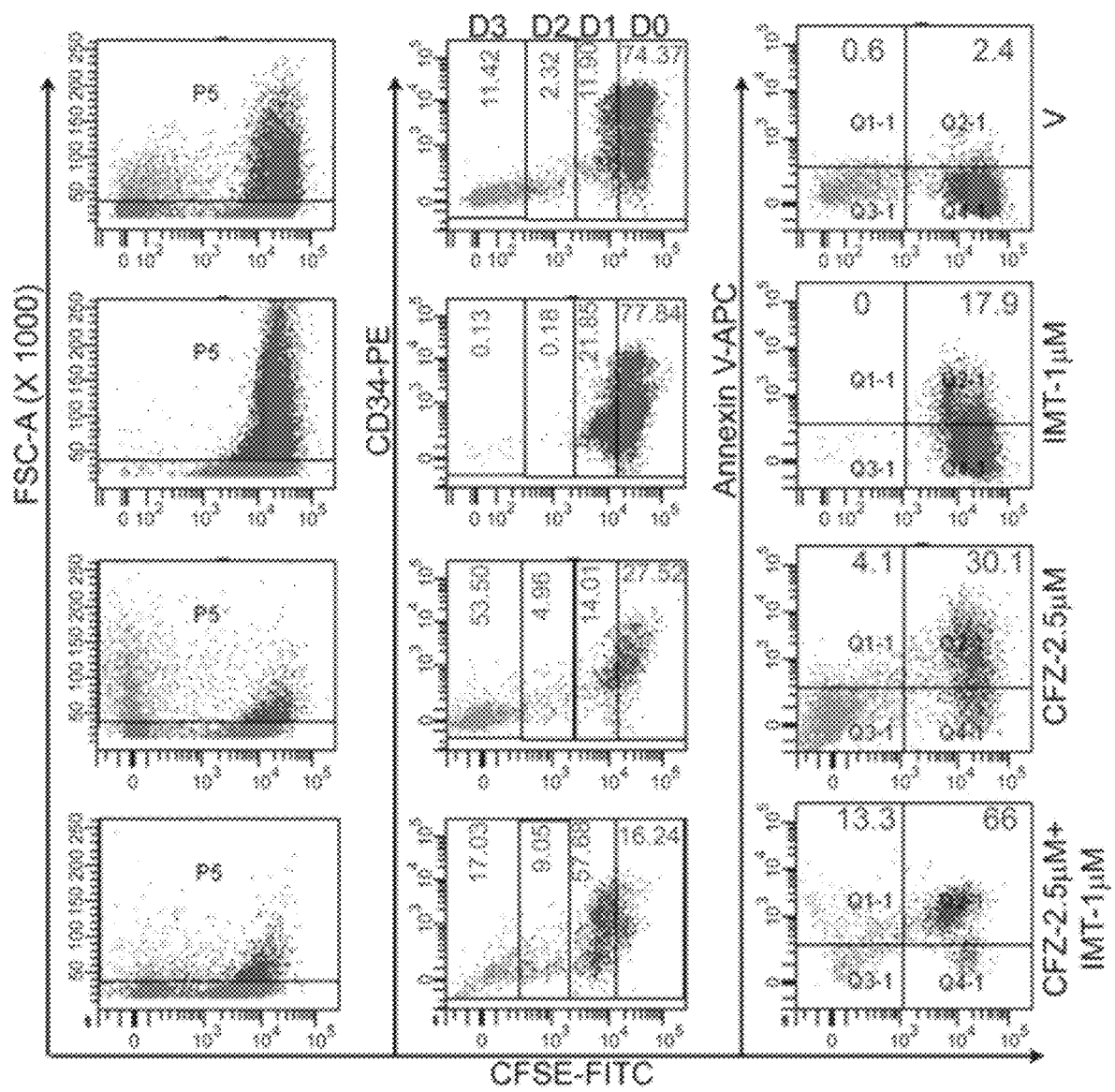
FIG. 5A-5C show CFZ reduces quiescent LSCs and in combination with imatinib nearly-obliterates them. CFZ alone or in combination with IMT reduces quiescent LSC population and induces apoptosis in these cells. CD34$^+$ population from imatinib-resistant CP-CML cells (n=3) were purified. Cells were then labeled with 2 M CFSE and treated as indicated (96 h). Cells were gated depending on CFSE intensity. Distribution (%) of CFSE/CD34$^+$ cells in each cell division is shown in different colored dots (D0-D3 represent cell division number). Apoptosis in these cells was determined by annexin V staining. (A) Representative dot plots corresponding to one patient (B) cell numbers (%) in D0-D3 from 3 patients plotted. (C) % mean apoptosis from 3 patients plotted. *,# p<0.05, ,## p<0.01, *,###, $$$p<0.0001. *V vs treatment, # IMT vs CFZ, $CFZ vs IMT+CFZ.
Figure 5B:
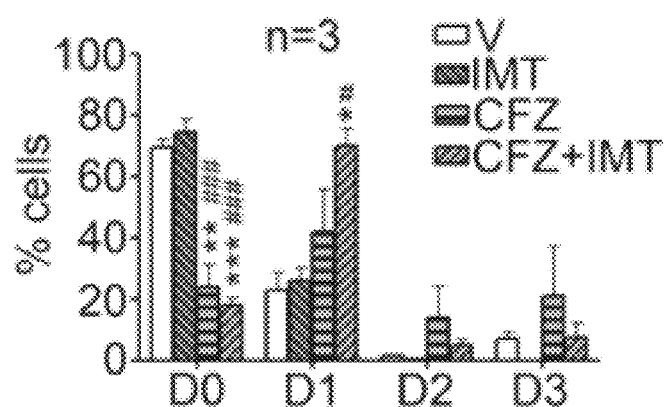

Example 5. CFZ Erodes Quiescent Cells Alone which is Exacerbated by Imatinib To assess the effect of CFZ on quiescent LSCs we labeled CD34+ cells from imatinib-resistant patients (n=3) with carboxyfluorescein succinimidyl ester (CFSE) and treated them with indicated drugs for 96 h. While imatinib failed to reduce CFSE-bright (non-dividing) cells, CFZ alone or in combination with imatinib drastically reduced their number and increased CFSE-dim (dividing cell) population (FIG. 5A-B). Evaluation of apoptosis in these cells revealed that CFZ alone caused robust apoptosis in both CFSE-bright and CFSE-dim cells while combination with imatinib caused their near-obliteration (FIGS. 5A and C).

Example 6. CFZ Alone or in Combination with Imatinib does not Affect Viability in CD34+ Cells from Healthy Donors Given its potent cytotoxic effect on CD34+ cells from CML patients we evaluated if CFZ also affected viability of CD34+ hematopoietic progenitor cells from healthy controls (HC). To such end CD34+ cells were isolated from 6 healthy volunteers and were treated with CFZ, IMT or IMT+CFZ as indicated for 48 h (FIG. 6A). No loss of survival was observed in any of the treatment groups (FIG. 6A). To further confirm it, CD34+ cells from one of the donors (HC11) was assessed for apoptosis by Annexin V and in this assay as well no apoptosis was observed in any of the treatment groups (FIG. 6B). These results indicate that cytotoxic effects of CFZ alone or in combination with IMT are specific for leukemia cells only.

Example 7. CFZ Increases the Bioavailability of Imatinib

Figure 5C:
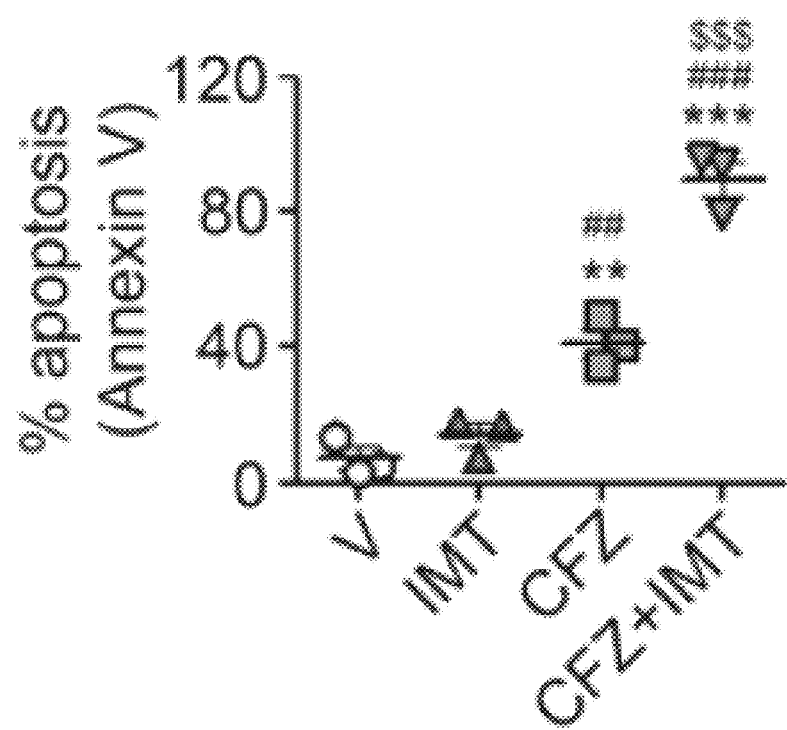

We next assessed if combination of CFZ and imatinib altered their bioavailability. For this SD rats (n=6 per group) were divided into 3 groups. The imatinib group (46.66 mg/kg imatinib mesylate; equivalent to human dose of 400 mg), the CFZ group (11.66 mg/kg CFZ; equivalent to human dose of 100 mg CFZ) and the combination group (IMT; 46.66 mg/kg and CFZ; 11.66 mg/kg) were orally administered indicated drugs following overnight fasting and blood samples were collected at 0.5, 1, 2, 4, 8, 12, 24, 48, 72, 96 and 120 hours. Plasma was separated and processed for analysis by LC-MS/MS. For pharmacokinetic and statistical analysis, plasma concentration versus time data were plotted and analyzed by non-compartmental analysis method using WinNonlin (Pharsight, Mountain View, Calif.) software. The plasma profile of both CFZ and imatinib in blood increased in combination group when compared to that of individual groups (higher AUC) (FIG. 5A-C). The increase was both due to increased absorption (higher $C_{max}$) and reduced excretion (lower clearance) (FIG. 5C). There was no change in $T_{max}$ specifying that the absorption pattern did not change (FIG. 5C). The increase in plasma profile of imatinib in presence of CFZ was 109.26%.

Example 8. CFZ and Imatinib as a Treatment Kit for CML or Drug-Resistant CML

From the above examples 1-7 it can be inferred that a treatment kit comprising of both TKIs (including but not limiting to imatinib and dasatinib) and CFZ tablets or capsules with a pamphlet containing instruction of use can be formulated. Such a kit may be consisting of both TKIs and clofazimine tablets or capsules in a single strip or individual strips (of CFZ and TKIs) containing instructions of use. Wherein, CFZ or a pharmaceutically acceptable salt thereof or a composition comprising CFZ and at least one pharmaceutically acceptable carrier or excipient is administered in a dose from 0.1 mg to 5000 mg, preferably from 0.5 to 1000, more preferably from 1 mg to 800 mg weekly or bi-weekly or daily or twice a day or three times a day or in still more divided doses in combination with TKIs including but not limiting to imatinib and dasatinib, wherein the dose of TKIs would be 0.1 mg-2000 mg, preferably from 10 mg-1800 mg, more preferably from 25 mg-1000 mg weekly or bi-weekly or daily or twice a day or three times a day or in still more divided doses.

Example 9. Pharmaceutical Formulation Comprising CFZ and TKIs for Treatment of CML or Drug-Resistant CML From the above examples 1-7 it can be inferred that a pharmaceutical formulation comprising both CFZ and TKIs (including but not limiting to imatinib and dasatinib) can be formulated wherein pharmaceutically acceptable composition of a combination of CFZ and TKIs (including but not limiting to imatinib and dasatinib) either or both are in the form of a suspension, liquid formulation, tablet, pill, capsule, powder or granule containing at least one of the following pharmaceutically acceptable excipient:
  (i) a diluent selected from the group consisting of lactose, mannitol, sorbitol, microcrystalline cellulose, sucrose, sodium citrate and dicalcium phosphate or a combination thereof;
  (ii) a binder selected from the group consisting of gum tragacanth, gum acacia, methyl cellulose, gelatin, polyvinyl pyrrolidone and starch or a combination thereof;
  (iii) a disintegrating agent selected from the group consisting of agar-agar, calcium carbonate, sodium carbonate, silicates, alginic acid, corn starch, potato tapioca starch and primogel or a combination thereof;
  (iv) a lubricant selected from the group consisting of magnesium stearate, calcium stearate, calcium steorotes, talc, solid polyethylene glycols and sodium lauryl sulphate or a combination thereof;
  (v) a glidant such as colloidal silicon dioxide;
  (vi) a sweetening agent selected from the group consisting of sucrose, saccharin and fructose or a combination thereof;
  (vii) a flavoring agent selected from the group consisting of peppermint, methyl salicylate, orange flavor and vanilla flavor or a combination thereof;
  (viii) a wetting agent selected from the group consisting of cetyl alcohol and glyceryl monostearate or a combination thereof;
  (ix) an absorbent selected from the group consisting of kaolin and bentonite clay or a combination thereof; and
  (x) a solution retarding agent selected from the group consisting of wax and paraffin or a combination thereof.

What is claimed is:

1. A method of treating chronic myeloid leukemia (CML) or drug resistant CML comprising, administering to human being or any other mammal or animal in need thereof, a therapeutically effective amount of Clofazimine (CFZ) or its pharmaceutically acceptable derivative, analogue, salt or composition; or a combination of a therapeutically effective amount of Clofazimine (CFZ) or its pharmaceutically acceptable derivative, analogue, salt or composition with a tyrosine kinase inhibitor (TKI).

2. The method of claim 1, wherein the tyrosine kinase inhibitor is selected from, but not limited to imatinib and dasatinib, or a pharmaceutically acceptable salt or a pharmaceutically acceptable composition thereof.

3. The method of claim 1, wherein the CFZ or its derivative, analogue, salt or composition is in a dose from 0.1 mg to 5000 mg or from 0.5 mg to 1000 mg, or from 1 mg to 800 mg weekly or bi-weekly or daily or twice a day or three times a day or in still more divided doses.

4. The method of claim 1, wherein the dose of TKIs is from 0.1 mg to 2000 mg, or from 10 mg to 1800 mg, or from 25 mg to 1000 mg weekly or bi-weekly or daily or twice a day or three times a day or in still more divided doses.

5. The method of claim 1, wherein CFZ induces apoptosis in CML cells and leukemia stem cells.

6. The method of claim 2, wherein CFZ synergizes the effect of imatinib and dasatinib in obliterating quiescent leukemia stem cells.

7. The method of claim 2, wherein CFZ increases the bioavailability of imatinib by about 109%.

8. The method of claim 1, wherein the CFZ or its derivative, analogue, salt or composition and/or the tyrosine kinase inhibitor (TKI) are administered by a route selected from oral, systemic, local, topical, intravenous, intra-arterial, intra-muscular, subcutaneous, intra-peritoneal, intra-dermal, buccal, intranasal, inhalation, vaginal, rectal, trans-dermal or a combination thereof.

9. The method of claim 1, wherein the pharmaceutically acceptable composition of CFZ or its pharmaceutically acceptable derivative, analogue or salt is in the form of a suspension, liquid formulation, tablet, pill, capsule, powder or granule, containing at least one of the following pharmaceutically acceptable excipients:
   (i) a diluent selected from the group consisting of lactose, mannitol, sorbitol, microcrystalline cellulose, sucrose, sodium citrate and dicalcium phosphate or a combination thereof;
   (ii) a binder selected from the group consisting of gum tragacanth, gum acacia, methyl cellulose, gelatin, polyvinyl pyrrolidone and starch or a combination thereof;
   (iii) a disintegrating agent selected from the group consisting of agar-agar, calcium carbonate, sodium carbonate, silicates, alginic acid, corn starch, potato tapioca starch and primogel or a combination thereof;
   (iv) a lubricant selected from the group consisting of magnesium stearate, calcium stearate, calcium steorotes, talc, solid polyethylene glycols and sodium lauryl sulphate or a combination thereof;
   (v) a glidant such as colloidal silicon dioxide;
   (vi) a sweetening agent selected from the group consisting of sucrose, saccharin and fructose or a combination thereof;
   (vii) a flavoring agent selected from the group consisting of peppermint, methyl salicylate, orange flavor and vanilla flavor or a combination thereof;
   (viii) a wetting agent selected from the group consisting of cetyl alcohol and glyceryl monostearate or a combination thereof;
   (ix) an absorbent selected from the group consisting of kaolin and bentonite clay or a combination thereof; and
   (x) a solution retarding agent selected from the group consisting of wax and paraffin or a combination thereof.

10. The method of claim 1, wherein the combination of CFZ or its pharmaceutically acceptable derivative, analogue or salt and tyrosine kinase inhibitor (TKI) is in a ratio of 1:4.

11. A combination comprising a therapeutically effective amount of Clofazimine (CFZ) or its pharmaceutically acceptable derivative, analogue, salt or composition and a tyrosine kinase inhibitor (TKI), or its pharmaceutically acceptable salt or composition, for treating chronic myeloid leukemia (CML) or drug resistant CML.

12. The combination of claim 11, wherein the tyrosine kinase inhibitor is selected from, but not limited to, imatinib and dasatinib, or a pharmaceutically acceptable salt or a pharmaceutically acceptable composition thereof.

13. The combination of claim 11, wherein the CFZ or its pharmaceutically acceptable derivative, analogue, salt or composition and TKI are in different unit doses.

14. A kit for treatment of chronic myeloid leukemia (CML) or drug resistant CML, the kit comprising:
   (i) a composition of clofazimine or its pharmaceutically acceptable analogue, derivative, or salt;
   (ii) a composition comprising one or more tyrosine kinase inhibitor(s); and
   (iii) a pamphlet containing instruction of use;
   wherein the pamphlet contains instructions that administration of said compositions in combination provides synergistic effect in comparison with the administration of either clofazimine or tyrosine kinase inhibitor(s) alone.

15. The kit of claim 14, wherein the composition (i) and composition (ii) are in single strip or separate strips.

16. The kit of claim 14, wherein the tyrosine kinase inhibitor is selected from imatinib, dasatinib or a combination thereof.

* * * * *